(12) United States Patent
Snyder et al.

(10) Patent No.: US 7,767,169 B2
(45) Date of Patent: Aug. 3, 2010

(54) ELECTRO-KINETIC AIR TRANSPORTER-CONDITIONER SYSTEM AND METHOD TO OXIDIZE VOLATILE ORGANIC COMPOUNDS

(75) Inventors: Gregory S. Snyder, Novato, CA (US); Andrew J. Parker, Novato, CA (US); Charles E. Taylor, Punta Gorda, FL (US)

(73) Assignee: Sharper Image Acquisition LLC, New York, NY (US)

( * ) Notice: Subject to any disclaimer, the term of this patent is extended or adjusted under 35 U.S.C. 154(b) by 1537 days.

(21) Appl. No.: 10/994,869

(22) Filed: Nov. 22, 2004

(65) Prior Publication Data
US 2005/0238551 A1 Oct. 27, 2005

Related U.S. Application Data

(60) Provisional application No. 60/528,908, filed on Dec. 11, 2003.

(51) Int. Cl.
*B01J 19/08* (2006.01)
(52) U.S. Cl. ............... 422/186.3; 422/186.04; 422/121; 96/96
(58) Field of Classification Search .......... 422/186.3, 422/186.04, 121; 96/96
See application file for complete search history.

(56) References Cited

U.S. PATENT DOCUMENTS

| 653,421 | A | 7/1900 | Lorey |
| 895,729 | A | 8/1908 | Carlborg |
| 995,958 | A | 6/1911 | Goldberg |
| 1,791,338 | A | 2/1931 | Wintermute |
| 1,869,335 | A | 7/1932 | Day |
| 1,882,949 | A | 10/1932 | Ruder |
| 2,129,783 | A | 9/1938 | Penney |
| 2,327,588 | A | 8/1943 | Bennett |

(Continued)

FOREIGN PATENT DOCUMENTS

CN 2111112 U 7/1972

(Continued)

OTHER PUBLICATIONS

U.S. Appl. No. 60/104,573, filed Oct. 16, 1998, Krichtafovitch.

(Continued)

*Primary Examiner*—Kishor Mayekar
(74) *Attorney, Agent, or Firm*—Arent Fox LLP

(57) ABSTRACT

Systems in accordance with embodiments of the present invention can include an air transporter-conditioner having a housing with an inlet and an outlet. An ion generator is disposed within the housing, the ion generator being adapted to create an airflow between the inlet and the outlet. The ion generator can comprise a emitter electrode array and a collector electrode array, with a voltage generator electrically connecting the arrays. A grid having a photocatalytic coating can further be disposed within the housing such that the grid is upstream of the arrays, and within an airflow generated by the ion generator. An activator, for example a UV lamp, can still further be disposed within the housing and upstream of the arrays, and positioned such that the grid is irradiated by UV light from the UV lamp, activating the photocatalyst and causing VOCs to breakdown in the presence of the photocatalyst.

68 Claims, 15 Drawing Sheets

U.S. PATENT DOCUMENTS

| | | |
|---|---|---|
| 2,359,057 A | 9/1944 | Skinner |
| 2,509,548 A | 5/1950 | White |
| 2,590,447 A | 3/1952 | Nord et al. |
| 2,949,550 A | 8/1960 | Brown |
| 3,018,394 A | 1/1962 | Brown |
| 3,026,964 A | 3/1962 | Penney |
| 3,374,941 A | 3/1968 | Okress |
| 3,518,462 A | 6/1970 | Brown |
| 3,540,191 A | 11/1970 | Herman |
| 3,581,470 A | 6/1971 | Aitkenhead et al. |
| 3,638,058 A | 1/1972 | Fritzius |
| 3,744,216 A | 7/1973 | Halloran |
| 3,806,763 A | 4/1974 | Masuda |
| 3,892,927 A | 7/1975 | Lindenberg |
| 3,945,813 A | 3/1976 | Iinoya et al. |
| 3,958,960 A | 5/1976 | Bakke |
| 3,958,961 A | 5/1976 | Bakke |
| 3,958,962 A | 5/1976 | Hayashi |
| 3,981,695 A | 9/1976 | Fuchs |
| 3,984,215 A | 10/1976 | Zucker |
| 3,988,131 A | 10/1976 | Kanazawa et al. |
| 4,007,024 A | 2/1977 | Sallee et al. |
| 4,052,177 A | 10/1977 | Kide |
| 4,056,372 A | 11/1977 | Hayashi |
| 4,070,163 A | 1/1978 | Kolb et al. |
| 4,074,983 A | 2/1978 | Bakke |
| 4,092,134 A | 5/1978 | Kikuchi |
| 4,097,252 A | 6/1978 | Kirchhoff et al. |
| 4,102,654 A | 7/1978 | Pellin |
| 4,104,042 A | 8/1978 | Brozenick |
| 4,110,086 A | 8/1978 | Schwab et al. |
| 4,119,415 A | 10/1978 | Hayashi et al. |
| 4,126,434 A | 11/1978 | Keiichi |
| 4,138,233 A | 2/1979 | Masuda |
| 4,147,522 A | 4/1979 | Gonas et al. |
| 4,155,792 A | 5/1979 | Gelhaar et al. |
| 4,171,975 A | 10/1979 | Kato et al. |
| 4,185,971 A | 1/1980 | Isahaya |
| 4,189,308 A | 2/1980 | Feldman |
| 4,205,969 A | 6/1980 | Matsumoto |
| 4,209,306 A | 6/1980 | Feldman et al. |
| 4,218,225 A | 8/1980 | Kirchhoff et al. |
| 4,225,323 A | 9/1980 | Zarchy et al. |
| 4,227,894 A | 10/1980 | Proynoff |
| 4,231,766 A | 11/1980 | Spurgin |
| 4,232,355 A | 11/1980 | Finger et al. |
| 4,244,710 A | 1/1981 | Burger |
| 4,244,712 A | 1/1981 | Tongret |
| 4,251,234 A | 2/1981 | Chang |
| 4,253,852 A | 3/1981 | Adams |
| 4,259,093 A | 3/1981 | Vlastos et al. |
| 4,259,452 A | 3/1981 | Yukuta et al. |
| 4,259,707 A | 3/1981 | Penney |
| 4,264,343 A | 4/1981 | Natarajan et al. |
| 4,266,948 A | 5/1981 | Teague et al. |
| 4,282,014 A | 8/1981 | Winkler et al. |
| 4,284,420 A | 8/1981 | Borysiak |
| 4,289,504 A | 9/1981 | Scholes |
| 4,293,319 A | 10/1981 | Claassen, Jr. |
| 4,308,036 A | 12/1981 | Zahedi et al. |
| 4,315,188 A | 2/1982 | Cerny et al. |
| 4,318,718 A | 3/1982 | Utsumi et al. |
| 4,338,560 A | 7/1982 | Lemley |
| 4,342,571 A | 8/1982 | Hayashi |
| 4,349,359 A | 9/1982 | Fitch et al. |
| 4,351,648 A | 9/1982 | Penney |
| 4,354,861 A | 10/1982 | Kalt |
| 4,357,150 A | 11/1982 | Masuda et al. |
| 4,362,632 A | 12/1982 | Jacob |
| 4,363,072 A | 12/1982 | Coggins |
| 4,366,525 A | 12/1982 | Baumgartner |
| 4,369,776 A | 1/1983 | Roberts |
| 4,375,364 A | 3/1983 | Van Hoesen et al. |
| 4,380,900 A | 4/1983 | Linder et al. |
| 4,386,395 A | 5/1983 | Francis, Jr. |
| 4,391,614 A | 7/1983 | Rozmus |
| 4,394,239 A | 7/1983 | Kitzelmann et al. |
| 4,405,342 A | 9/1983 | Bergman |
| 4,406,671 A | 9/1983 | Rozmus |
| 4,412,850 A | 11/1983 | Kurata et al. |
| 4,413,225 A | 11/1983 | Donig et al. |
| 4,414,603 A | 11/1983 | Masuda |
| 4,435,190 A | 3/1984 | Taillet et al. |
| 4,440,552 A | 4/1984 | Uchiya et al. |
| 4,443,234 A | 4/1984 | Carlsson |
| 4,445,911 A | 5/1984 | Lind |
| 4,477,263 A | 10/1984 | Shaver et al. |
| 4,477,268 A | 10/1984 | Kalt |
| 4,481,017 A | 11/1984 | Furlong |
| 4,496,375 A | 1/1985 | Levantine |
| 4,502,002 A | 2/1985 | Ando |
| 4,505,724 A | 3/1985 | Baab |
| 4,509,958 A | 4/1985 | Masuda et al. |
| 4,514,780 A | 4/1985 | Brussee et al. |
| 4,515,982 A | 5/1985 | Lechtken et al. |
| 4,516,991 A | 5/1985 | Kawashima |
| 4,521,229 A | 6/1985 | Baker et al. |
| 4,522,634 A | 6/1985 | Frank |
| 4,534,776 A | 8/1985 | Mammel et al. |
| 4,536,698 A | 8/1985 | Shevalenko et al. |
| 4,544,382 A | 10/1985 | Taillet et al. |
| 4,555,252 A | 11/1985 | Eckstein |
| 4,569,684 A | 2/1986 | Ibbott |
| 4,582,961 A | 4/1986 | Frederiksen |
| 4,587,475 A | 5/1986 | Finney, Jr. et al. |
| 4,588,423 A | 5/1986 | Gillingham et al. |
| 4,590,042 A | 5/1986 | Drage |
| 4,597,780 A | 7/1986 | Reif |
| 4,597,781 A | 7/1986 | Spector |
| 4,600,411 A | 7/1986 | Santamaria |
| 4,601,733 A | 7/1986 | Ordines et al. |
| 4,604,174 A | 8/1986 | Bollinger et al. |
| 4,614,573 A | 9/1986 | Masuda |
| 4,623,365 A | 11/1986 | Bergman |
| 4,626,261 A | 12/1986 | Jorgensen |
| 4,632,135 A | 12/1986 | Lenting et al. |
| 4,632,746 A | 12/1986 | Bergman |
| 4,636,981 A | 1/1987 | Ogura |
| 4,643,744 A | 2/1987 | Brooks |
| 4,643,745 A | 2/1987 | Sakakibara et al. |
| 4,647,836 A | 3/1987 | Olsen |
| 4,650,648 A | 3/1987 | Beer et al. |
| 4,656,010 A | 4/1987 | Leitzke et al. |
| 4,657,738 A | 4/1987 | Kanter et al. |
| 4,659,342 A | 4/1987 | Lind |
| 4,662,903 A | 5/1987 | Yanagawa |
| 4,666,474 A | 5/1987 | Cook |
| 4,668,479 A | 5/1987 | Manabe et al. |
| 4,670,026 A | 6/1987 | Hoenig |
| 4,673,416 A * | 6/1987 | Sakakibara et al. ............ 96/79 |
| 4,674,003 A | 6/1987 | Zylka |
| 4,680,496 A | 7/1987 | Letournel et al. |
| 4,686,370 A | 8/1987 | Blach |
| 4,689,056 A | 8/1987 | Noguchi et al. |
| 4,691,829 A | 9/1987 | Auer |
| 4,692,174 A | 9/1987 | Gelfand et al. |
| 4,693,869 A | 9/1987 | Pfaff |
| 4,694,376 A | 9/1987 | Gesslauer |
| 4,702,752 A | 10/1987 | Yanagawa |
| 4,713,092 A | 12/1987 | Kikuchi et al. |
| 4,713,093 A | 12/1987 | Hansson |
| 4,713,724 A | 12/1987 | Voelkel |
| 4,715,870 A | 12/1987 | Masuda et al. |
| 4,725,289 A | 2/1988 | Quintilian |

| | | | | | |
|---|---|---|---|---|---|
| 4,726,812 A | 2/1988 | Hirth | 5,210,678 A | 5/1993 | Lain et al. |
| 4,726,814 A | 2/1988 | Weitman | 5,215,558 A | 6/1993 | Moon |
| 4,736,127 A | 4/1988 | Jacobsen | 5,217,504 A | 6/1993 | Johansson |
| 4,743,275 A | 5/1988 | Flanagan | 5,217,511 A | 6/1993 | Plaks et al. |
| 4,749,390 A | 6/1988 | Burnett et al. | 5,234,555 A | 8/1993 | Ibbott |
| 4,750,921 A | 6/1988 | Sugita et al. | 5,248,324 A | 9/1993 | Hara |
| 4,760,302 A | 7/1988 | Jacobsen | 5,250,267 A | 10/1993 | Johnson et al. |
| 4,760,303 A | 7/1988 | Miyake | 5,254,155 A | 10/1993 | Mensi |
| 4,765,802 A | 8/1988 | Gombos et al. | 5,266,004 A | 11/1993 | Tsumurai et al. |
| 4,771,361 A | 9/1988 | Varga | 5,271,763 A | 12/1993 | Jang |
| 4,772,297 A | 9/1988 | Anzai | 5,282,891 A | 2/1994 | Durham |
| 4,779,182 A | 10/1988 | Mickal et al. | 5,290,343 A | 3/1994 | Morita et al. |
| 4,781,736 A | 11/1988 | Cheney et al. | 5,296,019 A | 3/1994 | Oakley et al. |
| 4,786,844 A | 11/1988 | Farrell et al. | 5,302,190 A | 4/1994 | Williams |
| 4,789,801 A | 12/1988 | Lee | 5,308,586 A | 5/1994 | Fritsche et al. |
| 4,808,200 A | 2/1989 | Dallhammer et al. | 5,315,838 A | 5/1994 | Thompson |
| 4,811,159 A | 3/1989 | Foster, Jr. | 5,316,741 A | 5/1994 | Sewell et al. |
| 4,822,381 A | 4/1989 | Mosley et al. | 5,330,559 A | 7/1994 | Cheney et al. |
| 4,853,005 A | 8/1989 | Jaisinghani et al. | 5,348,571 A | 9/1994 | Weber |
| 4,869,736 A | 9/1989 | Ivester et al. | 5,376,168 A | 12/1994 | Inculet |
| 4,892,713 A | 1/1990 | Newman | 5,378,978 A | 1/1995 | Gallo et al. |
| 4,929,139 A | 5/1990 | Vorreiter et al. | 5,386,839 A | 2/1995 | Chen |
| 4,940,470 A | 7/1990 | Jaisinghani et al. | 5,395,430 A | 3/1995 | Lundgren et al. |
| 4,940,894 A | 7/1990 | Morters | 5,401,301 A | 3/1995 | Schulmerich et al. |
| 4,941,068 A | 7/1990 | Hofmann | 5,401,302 A | 3/1995 | Schulmerich et al. |
| 4,941,224 A | 7/1990 | Saeki et al. | 5,403,383 A | 4/1995 | Jaisinghani |
| 4,944,778 A | 7/1990 | Yanagawa | 5,405,434 A | 4/1995 | Inculet |
| 4,954,320 A | 9/1990 | Birmingham et al. | 5,407,469 A | 4/1995 | Sun |
| 4,955,991 A | 9/1990 | Torok et al. | 5,407,639 A | 4/1995 | Watanabe et al. |
| 4,966,666 A | 10/1990 | Waltonen | 5,417,936 A | 5/1995 | Suzuki et al. |
| 4,967,119 A | 10/1990 | Torok et al. | 5,419,953 A | 5/1995 | Chapman |
| 4,976,752 A | 12/1990 | Torok et al. | 5,433,772 A | 7/1995 | Sikora |
| 4,978,372 A | 12/1990 | Pick | 5,435,817 A | 7/1995 | Davis et al. |
| D315,598 S | 3/1991 | Yamamoto et al. | 5,435,978 A | 7/1995 | Yokomi |
| 5,003,774 A | 4/1991 | Leonard | 5,437,713 A | 8/1995 | Chang |
| 5,006,761 A | 4/1991 | Torok et al. | 5,437,843 A | 8/1995 | Kuan |
| 5,010,869 A | 4/1991 | Lee | 5,445,798 A | 8/1995 | Ikeda et al. |
| 5,012,093 A | 4/1991 | Shimizu | 5,466,279 A | 11/1995 | Hattori et al. |
| 5,012,094 A | 4/1991 | Hamade | 5,468,454 A | 11/1995 | Kim |
| 5,012,159 A | 4/1991 | Torok et al. | 5,474,599 A | 12/1995 | Cheney et al. |
| 5,022,979 A | 6/1991 | Hijikata et al. | 5,484,472 A | 1/1996 | Weinberg |
| 5,024,685 A | 6/1991 | Torok et al. | 5,484,473 A | 1/1996 | Bontempi |
| 5,030,254 A | 7/1991 | Heyen et al. | 5,492,678 A | 2/1996 | Ota et al. |
| 5,034,033 A | 7/1991 | Alsup et al. | 5,501,844 A | 3/1996 | Kasting, Jr. et al. |
| 5,037,456 A | 8/1991 | Yu | 5,503,808 A | 4/1996 | Garbutt et al. |
| 5,045,095 A | 9/1991 | You | 5,503,809 A | 4/1996 | Coate et al. |
| 5,053,912 A | 10/1991 | Loreth et al. | 5,505,914 A | 4/1996 | Tona-Serra |
| 5,059,219 A | 10/1991 | Plaks et al. | 5,508,008 A | 4/1996 | Wasser |
| 5,061,462 A | 10/1991 | Suzuki | 5,514,345 A | 5/1996 | Garbutt et al. |
| 5,066,313 A | 11/1991 | Mallory, Sr. | 5,516,493 A | 5/1996 | Bell et al. |
| 5,072,746 A | 12/1991 | Kantor | 5,518,531 A | 5/1996 | Joannu |
| 5,076,820 A | 12/1991 | Gurvitz | 5,520,887 A | 5/1996 | Shimizu et al. |
| 5,077,468 A | 12/1991 | Hamade | 5,525,310 A | 6/1996 | Decker et al. |
| 5,077,500 A | 12/1991 | Torok et al. | 5,529,613 A | 6/1996 | Yavnieli |
| 5,100,440 A | 3/1992 | Stahel et al. | 5,529,760 A | 6/1996 | Burris |
| RE33,927 E | 5/1992 | Fuzimura | 5,532,798 A | 7/1996 | Nakagami et al. |
| D326,514 S | 5/1992 | Alsup et al. | 5,535,089 A | 7/1996 | Ford et al. |
| 5,118,942 A | 6/1992 | Hamade | 5,536,477 A | 7/1996 | Cha et al. |
| 5,125,936 A | 6/1992 | Johansson | 5,538,695 A | 7/1996 | Shinjo et al. |
| 5,136,461 A | 8/1992 | Zellweger | 5,540,761 A | 7/1996 | Yamamoto |
| 5,137,546 A | 8/1992 | Steinbacher et al. | 5,542,967 A | 8/1996 | Ponizovsky et al. |
| 5,141,529 A | 8/1992 | Oakley et al. | 5,545,379 A | 8/1996 | Gray |
| 5,141,715 A | 8/1992 | Sackinger et al. | 5,545,380 A | 8/1996 | Gray |
| D329,284 S | 9/1992 | Patton | 5,547,643 A | 8/1996 | Nomoto et al. |
| 5,147,429 A | 9/1992 | Bartholomew et al. | 5,549,874 A | 8/1996 | Kimiya et al. |
| 5,154,733 A | 10/1992 | Fujii et al. | 5,554,344 A | 9/1996 | Duarte |
| 5,158,580 A | 10/1992 | Chang | 5,554,345 A | 9/1996 | Kitchenman |
| D332,655 S | 1/1993 | Lytle et al. | 5,569,368 A | 10/1996 | Larsky et al. |
| 5,180,404 A | 1/1993 | Loreth et al. | 5,569,437 A | 10/1996 | Stiehl et al. |
| 5,183,480 A | 2/1993 | Raterman et al. | D375,546 S | 11/1996 | Lee |
| 5,196,171 A | 3/1993 | Peltier | 5,571,483 A | 11/1996 | Pfingstl et al. |
| 5,198,003 A | 3/1993 | Haynes | 5,573,577 A | 11/1996 | Joannou |
| 5,199,257 A | 4/1993 | Colletta et al. | 5,573,730 A | 11/1996 | Gillum |

| | | | | | | |
|---|---|---|---|---|---|---|
| 5,578,112 | A | 11/1996 | Krause | D449,679 | S | 10/2001 | Smith et al. |
| 5,578,280 | A | 11/1996 | Kazi et al. | 6,296,692 | B1 | 10/2001 | Gutmann |
| 5,582,632 | A | 12/1996 | Nohr et al. | 6,302,944 | B1 | 10/2001 | Hoenig |
| 5,587,131 | A | 12/1996 | Malkin et al. | 6,309,514 | B1 | 10/2001 | Conrad et al. |
| D377,523 | S | 1/1997 | Marvin et al. | 6,312,507 | B1 | 11/2001 | Taylor et al. |
| 5,591,253 | A | 1/1997 | Altman et al. | 6,315,821 | B1 | 11/2001 | Pillion et al. |
| 5,591,334 | A | 1/1997 | Shimizu et al. | 6,328,791 | B1 | 12/2001 | Pillion et al. |
| 5,591,412 | A | 1/1997 | Jones et al. | 6,348,103 | B1 | 2/2002 | Ahlborn et al. |
| 5,593,476 | A | 1/1997 | Coppom | 6,350,417 | B1 | 2/2002 | Lau et al. |
| 5,601,636 | A | 2/1997 | Glucksman | 6,362,604 | B1 | 3/2002 | Cravey |
| 5,603,752 | A | 2/1997 | Hara | 6,368,668 | B1 * | 4/2002 | Kobayashi et al. ........ 427/376.2 |
| 5,603,893 | A | 2/1997 | Gundersen et al. | 6,372,097 | B1 | 4/2002 | Chen |
| 5,614,002 | A | 3/1997 | Chen | 6,373,723 | B1 | 4/2002 | Wallgren et al. |
| 5,624,476 | A | 4/1997 | Eyraud | 6,379,427 | B1 | 4/2002 | Siess |
| 5,630,866 | A | 5/1997 | Gregg | 6,391,259 | B1 | 5/2002 | Malkin et al. |
| 5,630,990 | A | 5/1997 | Conrad et al. | 6,398,852 | B1 | 6/2002 | Loreth |
| 5,637,198 | A | 6/1997 | Breault | 6,447,587 | B1 | 9/2002 | Pillion et al. |
| 5,637,279 | A | 6/1997 | Besen et al. | 6,451,266 | B1 | 9/2002 | Lau et al. |
| 5,641,342 | A | 6/1997 | Smith et al. | 6,464,754 | B1 | 10/2002 | Ford |
| 5,641,461 | A | 6/1997 | Ferone | 6,471,753 | B1 | 10/2002 | Ahn et al. |
| 5,647,890 | A | 7/1997 | Yamamoto | 6,494,940 | B1 | 12/2002 | Hak |
| 5,648,049 | A | 7/1997 | Jones et al. | 6,504,308 | B1 | 1/2003 | Krichtafovitch et al. |
| 5,655,210 | A | 8/1997 | Gregoire et al. | 6,508,982 | B1 | 1/2003 | Shoji |
| 5,656,063 | A | 8/1997 | Hsu | 6,544,485 | B1 | 4/2003 | Taylor |
| 5,665,147 | A | 9/1997 | Taylor et al. | 6,585,935 | B1 | 7/2003 | Taylor et al. |
| 5,667,563 | A | 9/1997 | Silva, Jr. | 6,588,434 | B2 | 7/2003 | Taylor et al. |
| 5,667,564 | A | 9/1997 | Weinberg | 6,603,268 | B2 | 8/2003 | Lee |
| 5,667,565 | A | 9/1997 | Gondar | 6,607,702 | B1 | 8/2003 | Kang et al. |
| 5,667,756 | A | 9/1997 | Ho | 6,613,277 | B1 | 9/2003 | Monagan |
| 5,669,963 | A | 9/1997 | Horton et al. | 6,632,407 | B1 | 10/2003 | Lau et al. |
| 5,678,237 | A | 10/1997 | Powell et al. | 6,635,105 | B2 | 10/2003 | Ahlborn et al. |
| 5,681,434 | A | 10/1997 | Eastlund | 6,672,315 | B2 | 1/2004 | Taylor et al. |
| 5,681,533 | A | 10/1997 | Hiromi | 6,679,940 | B1 * | 1/2004 | Oda ............................. 96/55 |
| 5,698,164 | A | 12/1997 | Kishioka et al. | 6,709,484 | B2 | 3/2004 | Lau et al. |
| 5,702,507 | A | 12/1997 | Wang | 6,713,026 | B2 | 3/2004 | Taylor et al. |
| D389,567 | S | 1/1998 | Gudefin | 6,735,830 | B1 | 5/2004 | Merciel |
| 5,766,318 | A | 6/1998 | Loreth et al. | 6,749,667 | B2 | 6/2004 | Reeves et al. |
| 5,779,769 | A | 7/1998 | Jiang | 6,753,652 | B2 | 6/2004 | Kim |
| 5,814,135 | A | 9/1998 | Weinberg | 6,761,796 | B2 | 7/2004 | Srivastava et al. |
| 5,835,840 | A | 11/1998 | Goswani | 6,768,108 | B2 | 7/2004 | Hirano et al. |
| 5,879,435 | A | 3/1999 | Satyapal et al. | 6,768,110 | B2 | 7/2004 | Alani |
| 5,893,977 | A | 4/1999 | Pucci | 6,768,120 | B2 | 7/2004 | Leung et al. |
| 5,911,957 | A | 6/1999 | Khatchatrian et al. | 6,768,121 | B2 | 7/2004 | Horskey |
| 5,972,076 | A | 10/1999 | Nichols et al. | 6,770,878 | B2 | 8/2004 | Uhlemann et al. |
| 5,975,090 | A | 11/1999 | Taylor et al. | 6,773,682 | B1 * | 8/2004 | Benda ..................... 422/186.3 |
| 5,980,614 | A | 11/1999 | Loreth et al. | 6,774,359 | B1 | 8/2004 | Hirabayashi et al. |
| 5,993,521 | A | 11/1999 | Loreth et al. | 6,777,686 | B2 | 8/2004 | Olson et al. |
| 5,993,738 | A | 11/1999 | Goswani | 6,777,699 | B1 | 8/2004 | Miley et al. |
| 5,997,619 | A | 12/1999 | Knuth et al. | 6,777,882 | B2 | 8/2004 | Goldberg et al. |
| 6,019,815 | A | 2/2000 | Satyapal et al. | 6,781,136 | B1 | 8/2004 | Kato |
| 6,042,637 | A | 3/2000 | Weinberg | 6,785,912 | B1 | 9/2004 | Julio |
| 6,063,168 | A | 5/2000 | Nichols et al. | 6,791,814 | B2 | 9/2004 | Adachi et al. |
| 6,086,657 | A | 7/2000 | Freije | 6,794,661 | B2 | 9/2004 | Tsukihara et al. |
| 6,117,216 | A | 9/2000 | Loreth | 6,797,339 | B2 | 9/2004 | Akizuki et al. |
| 6,118,645 | A | 9/2000 | Partridge | 6,797,964 | B2 | 9/2004 | Yamashita |
| 6,126,722 | A | 10/2000 | Mitchell et al. | 6,799,068 | B1 | 9/2004 | Hartmann et al. |
| 6,126,727 | A | 10/2000 | Lo | 6,800,862 | B2 | 10/2004 | Matsumoto et al. |
| 6,149,717 | A * | 11/2000 | Satyapal et al. ................ 96/16 | 6,803,585 | B2 | 10/2004 | Glukhoy |
| 6,149,815 | A | 11/2000 | Sauter | 6,805,916 | B2 | 10/2004 | Cadieu |
| 6,152,146 | A | 11/2000 | Taylor et al. | 6,806,035 | B1 | 10/2004 | Atireklapvarodom et al. |
| 6,163,098 | A | 12/2000 | Taylor et al. | 6,806,163 | B2 | 10/2004 | Wu et al. |
| 6,176,977 | B1 | 1/2001 | Taylor et al. | 6,806,468 | B2 | 10/2004 | Laiko et al. |
| 6,182,461 | B1 | 2/2001 | Washburn et al. | 6,808,606 | B2 | 10/2004 | Thomsen et al. |
| 6,182,671 | B1 | 2/2001 | Taylor et al. | 6,809,310 | B2 | 10/2004 | Chen |
| 6,193,852 | B1 | 2/2001 | Caracciolo et al. | 6,809,312 | B1 | 10/2004 | Park et al. |
| 6,203,600 | B1 | 3/2001 | Loreth | 6,809,325 | B2 | 10/2004 | Dahl et al. |
| 6,212,883 | B1 | 4/2001 | Kang | 6,812,647 | B2 | 11/2004 | Cornelius |
| 6,228,149 | B1 | 5/2001 | Alenichev et al. | 6,815,690 | B2 | 11/2004 | Veerasamy et al. |
| 6,252,012 | B1 | 6/2001 | Egitto et al. | 6,818,257 | B2 | 11/2004 | Amann et al. |
| 6,270,733 | B1 | 8/2001 | Rodden | 6,818,909 | B2 | 11/2004 | Murrell et al. |
| 6,277,248 | B1 | 8/2001 | Ishioka et al. | 6,819,053 | B2 | 11/2004 | Johnson |
| 6,282,106 | B2 | 8/2001 | Grass | 6,861,036 | B2 * | 3/2005 | Biswas et al. .......... 422/186.04 |
| D449,097 | S | 10/2001 | Smith et al. | 6,863,869 | B2 | 3/2005 | Taylor et al. |

| | | | |
|---|---|---|---|
| 6,896,853 B2 | 5/2005 | Law et al. | |
| 6,911,186 B2 | 6/2005 | Taylor et al. | |
| 2001/0048906 A1 | 12/2001 | Lau et al. | |
| 2002/0069760 A1 | 6/2002 | Pruette et al. | |
| 2002/0079212 A1 | 6/2002 | Taylor et al. | |
| 2002/0098131 A1 | 7/2002 | Taylor et al. | |
| 2002/0122751 A1 | 9/2002 | Sinaiko et al. | |
| 2002/0122752 A1 | 9/2002 | Taylor et al. | |
| 2002/0127156 A1 | 9/2002 | Taylor | |
| 2002/0134664 A1 | 9/2002 | Taylor et al. | |
| 2002/0134665 A1 | 9/2002 | Taylor et al. | |
| 2002/0141914 A1 | 10/2002 | Lau et al. | |
| 2002/0144601 A1 | 10/2002 | Palestro et al. | |
| 2002/0146356 A1 | 10/2002 | Sinaiko et al. | |
| 2002/0150520 A1 | 10/2002 | Taylor et al. | |
| 2002/0152890 A1 | 10/2002 | Leiser | |
| 2002/0155041 A1 | 10/2002 | McKinney, Jr. et al. | |
| 2002/0170435 A1 | 11/2002 | Joannou | |
| 2002/0190658 A1 | 12/2002 | Lee | |
| 2002/0195951 A1 | 12/2002 | Lee | |
| 2003/0005824 A1 | 1/2003 | Katou et al. | |
| 2003/0050196 A1 | 3/2003 | Hirano et al. | |
| 2003/0170150 A1 | 9/2003 | Law et al. | |
| 2003/0206837 A1 | 11/2003 | Taylor et al. | |
| 2003/0206839 A1 | 11/2003 | Taylor et al. | |
| 2003/0206840 A1 | 11/2003 | Taylor et al. | |
| 2004/0033176 A1 | 2/2004 | Lee et al. | |
| 2004/0052700 A1 | 3/2004 | Kotlyar et al. | |
| 2004/0065202 A1 | 4/2004 | Gatchell et al. | |
| 2004/0096376 A1 | 5/2004 | Taylor | |
| 2004/0136863 A1 | 7/2004 | Yates et al. | |
| 2004/0166037 A1 | 8/2004 | Youdell et al. | |
| 2004/0226447 A1 | 11/2004 | Lau et al. | |
| 2004/0234431 A1 | 11/2004 | Taylor et al. | |
| 2004/0237787 A1 | 12/2004 | Reeves et al. | |
| 2004/0251124 A1 | 12/2004 | Lau | |
| 2004/0251909 A1 | 12/2004 | Taylor et al. | |
| 2005/0000793 A1 | 1/2005 | Taylor et al. | |

FOREIGN PATENT DOCUMENTS

| | | |
|---|---|---|
| CN | 87210843 U | 7/1988 |
| CN | 2138764 Y | 6/1993 |
| CN | 2153231 Y | 12/1993 |
| DE | 2206057 | 8/1973 |
| DE | 197 41 621 C 1 | 6/1999 |
| EP | 0433152 A1 | 12/1990 |
| EP | 0332624 B1 | 1/1992 |
| FR | 2690509 | 10/1993 |
| GB | 643363 | 9/1950 |
| JP | S51-90077 | 8/1976 |
| JP | S62-20653 | 2/1987 |
| JP | S63-164948 | 10/1988 |
| JP | 10137007 | 5/1998 |
| JP | 11-114443 A * | 4/1999 |
| JP | 11104223 | 4/1999 |
| JP | 2000236914 | 9/2000 |
| WO | WO 92/05875 A1 | 4/1992 |
| WO | WO 96/04703 A1 | 2/1996 |
| WO | WO 99/07474 A1 | 2/1999 |
| WO | WO 00/10713 A1 | 3/2000 |
| WO | WO 01/47803 A1 | 7/2001 |
| WO | WO 01/48781 A1 | 7/2001 |
| WO | WO 01/64349 A1 | 9/2001 |
| WO | WO 01/85348 A2 | 11/2001 |
| WO | WO 02/20162 A2 | 3/2002 |
| WO | WO 02/20163 A2 | 3/2002 |
| WO | WO 02/30574 A1 | 4/2002 |
| WO | WO 02/32578 A1 | 4/2002 |
| WO | WO 02/42003 A1 | 5/2002 |
| WO | WO 02/066167 A1 | 8/2002 |
| WO | WO 03/009944 A1 | 2/2003 |
| WO | WO 03/013620 A1 | 2/2003 |
| WO | WO 03/013734 AA | 2/2003 |

OTHER PUBLICATIONS

U.S. Appl. No. 60/306,479, filed Jul. 18, 2001, Taylor.
U.S. Appl. No. 60/341,179, filed Dec. 13, 2001, Taylor et al.
U.S. Appl. No. 60/340,702, filed Dec. 13, 2001, Taylor et al.
U.S. Appl. No. 60/341,377, filed Dec. 13, 2001, Taylor et al.
U.S. Appl. No. 60/341,518, filed Dec. 13, 2001, Taylor.
U.S. Appl. No. 60/340,288, filed Dec. 13, 2001, Taylor.
U.S. Appl. No. 60/341,176, filed Dec. 13, 2001, Taylor.
U.S. Appl. No. 60/340,462, filed Dec. 13, 2001, Taylor.
U.S. Appl. No. 60/340,090, filed Dec. 13, 2001, Taylor.
U.S. Appl. No. 60/341,433, filed Dec. 13, 2001, Taylor.
U.S. Appl. No. 60/341,592, filed Dec. 13, 2001, Taylor.
U.S. Appl. No. 60/341,320, filed Dec. 13, 2001, Taylor.
U.S. Appl. No. 60/391,070, filed Jun. 6, 2002, Reeves.
Blueair AV 402 Air Purifier, http://www.air-purifiers-usa.biz/Blueair_AV402.htm, 4 pp., 1996.
Blueair AV 501 Air Purifier, http://www.air-purifiers-usa.biz/Blueair_AV501.htm, 15 pp., 1997.
ConsumerReports.org, "Air Cleaners: Behind the Hype," http://www.consumerreports.org/main/content/printable.jsp?FOLDER%3C%3EFOLDER_id, Oct. 2003, 6 pp.
Electrical schematic and promotional material available from Zenion Industries, 7 pages, Aug. 1990.
English Translation of German Patent Document DE 197 41 621 C1; Publication Date: Jun. 10, 1999.
English Translation of German Published Patent Application 2206057; Publication Date: Aug. 16, 1973.
English Translation of Japanese Unexamined Patent Application Bulletin No. S51-90077; Publication Date: Aug. 6, 1976.
English Translation of Japanese Unexamined Utility Model Application No. S62-20653; Publication Date: Feb. 7, 1987.
English Translation of Japanese Unexamined Utility Model Application No. S63-164948; Publication Date: Oct. 27, 1988.
Friedrich C-90A Electronic Air Cleaner, Service Information, Friedrich Air Conditioning Co., 12 pp., 1985.
Friedrich C-90A, "How the C-90A Works," BestAirCleaner.com http://www.bestaircleaner.com/faq/c90works.asp, 1 page.
"Household Air Cleaners," Consumer Reports Magazine, Oct. 1992, 6 pp.
LakeAir Excel and Maxum Portable Electronic Air Cleaners, Operating and Service Manual, LakeAir International, Inc., 11 pp., 1971.
LENTEK Sila™ Plug-In Air Purifier/Deodorizer product box copyrighted 1999, 13 pages.
Promotional material available from Zenion Industries for the Plasma-Pure 100/200/300, 2 pages, Aug. 1990.
Promotional material available from Zenion Industries for the Plasma-Tron, 2 pages, Aug. 1990.
Trion 120 Air Purifier, Model 442501-025, http://www.feddersoutled.com/trion120.html, 16 pp., believed to be at least one year prior to Nov. 5, 1998.
Trion 150 Air Purifier, Model 45000-002, http://www.feddersoutlet.com/trion150.html, 11 pp., believed to be at least one year prior to Nov. 5, 1998.
Trion 350 Air Purifier, Model 450111-010, http://www.feddersoutlet.com/trion350.html, 12 pp., believed to be at least one year prior to Nov. 5, 1998.
Trion Console 250 Electronic Air Cleaner, Model Series 442857 and 445600, Manual for Installation•Operation•Maintenance, Trion Inc., 7 pp., believed to be at least one year prior to Nov. 5, 1998.

* cited by examiner

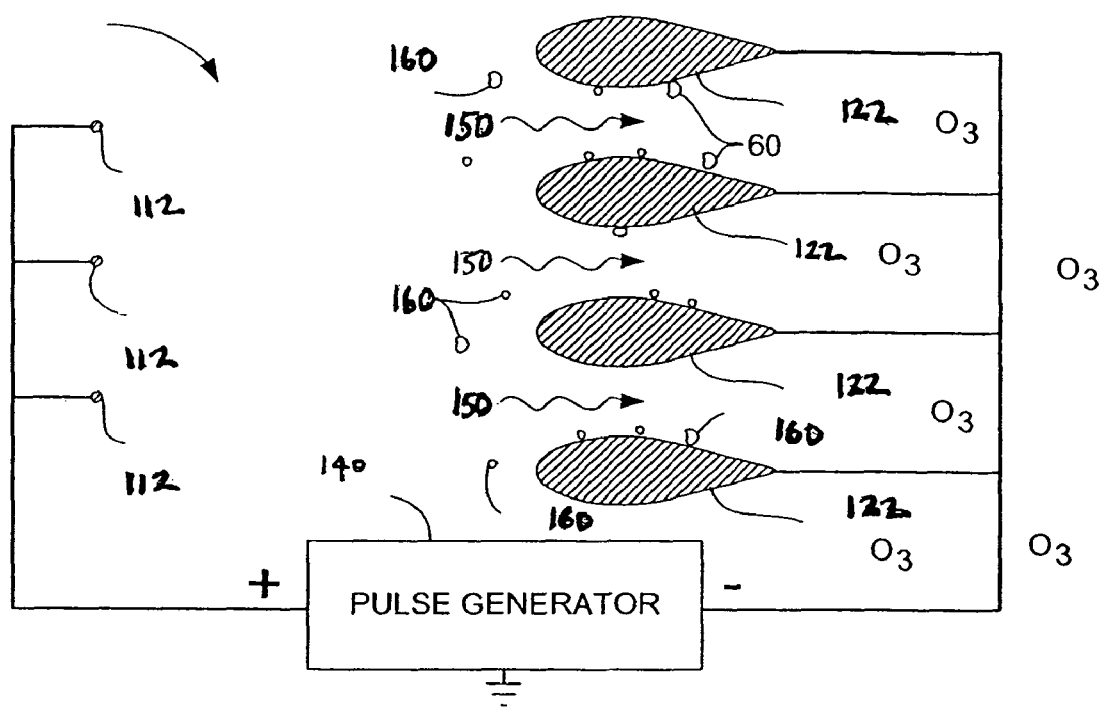
FIG. - 1    (PRIOR ART)

ELECTRO-KINETIC AIR TRANSPORTER-CONDITIONER SYSTEM AND METHOD TO OXIDIZE VOLATILE ORGANIC COMPOUNDS

CLAIM OF PRIORITY

This application claims priority from U.S. Provisional Patent Application No. 60/528,908 entitled "Electro-Kinetic Air Transporter-Conditioner System and Method to Oxidize Volatile Organic Compounds" by Snyder, et al., filed Dec. 11, 2003 and incorporated herein by reference.

CROSS-REFERENCE TO RELATED ART

The present invention is related to the following patent applications and patent, each of which is incorporated herein by reference:

U.S. patent application Ser. No. 10/074,207, now abandoned, filed Feb. 12, 2002, entitled "Electro-Kinetic Air Transporter-Conditioner Devices with Interstitial Electrode";

U.S. patent application Ser. No. 10/074,347, now U.S. Pat. No. 6,911,186, filed Feb. 12, 2002, "Electro-Kinetic Air Transporter and Conditioner Device with Enhanced Housing Configuration and Enhanced Anti-Microorganism Capability";

U.S. patent application Ser. No. 10/717,420, now abandoned, filed Nov. 19, 2003, "Electro-Kinetic Air Transporter and Conditioner Devices with Insulated Driver Electrodes";

U.S. patent application Ser. No. 10/774,579, now U.S. Pat. No. 7,077,890, filed Feb. 9, 2004, "Electrostatic Precipitators with Insulated Driver Electrodes"; and U.S. Pat. No. 6,176,977, entitled "Electro-Kinetic Air Transporter-Conditioner".

TECHNICAL FIELD

The present invention relates generally to ion generating devices that produce an electro-kinetic flow of air from which particulate matter is removed.

BACKGROUND

It is known in the art to produce an airflow using electro-kinetic techniques, by which electrical power is converted into a flow of air without mechanically moving components. One such system is described in U.S. Pat. No. 4,789,801 issued to Lee (1988), depicted herein in simplified form as FIG. 1 and which patent is incorporated herein by reference. The system 100 includes an array of first ("emitter") electrodes or conductive surfaces 112 that are spaced-apart symmetrically from an array of second ("collector") electrodes or conductive surfaces 122. As shown the emitter array includes a single emitter electrode, but emitter arrays 110 having multiple emitter electrodes 112 are also described by Lee.

In this example, the positive terminal of a generator (e.g. a pulse generator) is coupled to the emitter electrodes, and the negative terminal of the generator is coupled to the collector electrodes. The pulse generator 140 outputs a train of high voltage pulses (e.g., 0 to perhaps +5 KV). The high voltage pulses ionize the air between the emitter and collector electrodes 112/122, and create airflow 150 from the emitter electrodes 112 toward the collector electrodes 122. Particulate matter 160 is entrained within the airflow 150 and also moves towards the collector electrodes 122. Much of the particulate matter 160 is electrostatically attracted to the surfaces of the collector electrodes 122, where the particulate matter 160 can collect, thus conditioning airflow 150 exiting the system 100. As a further benefit, the high voltage field present between the electrodes can release ozone into the ambient environment, which can eliminate odors that are entrained in the airflow.

In addition to particulate matter, volatile organic compounds (VOCs) can commonly be found in air. VOCs are petroleum-based chemicals found at elevated levels in most houses. Thousands of possible VOCs outgas from common household products. For example, VOCs can be released into the air by synthetic fragrances (as found in soaps, candles, air fresheners, incense and potpourri), paint, carpet, furnishings, glues, plastics, pressed wood products (such as plywood and particle board), and even fresh flowers and other items. Formaldehyde is a VOC that can be a particular problem in a home. Formaldehyde can be found in building materials, caulks and adhesives, paint, furniture, etc. When exposed to formaldehyde, it is not uncommon for a person to experience headaches, numbness or tingling of extremities, brain fog and inability to concentrate, anxiety, depression, etc. Further, formaldehyde is a sensitizing substance that can lower a person's threshold of sensitivity to other chemicals. Outgassing can be diluted by improving ventilation; however, where a source of formaldehyde and/or other VOCs is organic matter, such as mold, outgassing can be continuous and persistent. VOCs as outgassed waste products of mold can be more dangerous to an individual's health than mold spores drifting through the air.

In addition to producing side-effects in a sensitive individual, VOCs can produce noticeable odors. For example, the treatment process for many municipal water sources includes the addition of chlorine dioxide for use as a disinfectant. When a tap is turned on, the chlorine dioxide can diffuse into the air as the water is running. The chlorine dioxide can combine with VOCs found in the ambient air to produce compounds having unpleasant odors. The higher the levels of VOCs and chlorine dioxide, the higher the potential for odors. An odor problem will persist until VOC levels decrease. In enclosed areas with little ventilation, such as laundry rooms, basements, bathrooms and closets, such compounds accumulate, causing odors to be stronger and to linger longer than in well-ventilated areas.

One solution to VOC contamination is to clean and scrub air of VOCs. In air purifiers, air can be drawn through the purifier using fans and moved proximate to or through one or more carbon filters which absorb VOCs and odors. For example, a device using a high-efficiency particulate arrester (HEPA) filter typically draws large amounts of air through the HEPA filter using powerful fans. HEPA filters collect significant amounts of large particulate matter (0.3 µm and above) and can be coupled with a carbon filter that absorbs VOCs (and odors), removing VOCs from air passing through the HEPA filter. Such air purifiers can have limited effectiveness, however. The HEPA filter can have trouble collecting particulate matter smaller than 0.3 µm, and the carbon filter coupled with the HEPA filter eventually saturates and begins dumping VOCs and odors back into the environment.

Accordingly, there is a desire to improve upon existing electro-kinetic techniques by enabling existing electro-kinetic techniques to remove VOCs from air.

BRIEF DESCRIPTION OF THE FIGURES

Further details of embodiments of the present invention are explained with the help of the attached drawings in which:

FIG. 1 is a schematic of an electrode assembly for use in an air transporter-conditioner system according to the prior art;

DETAILED DESCRIPTION

Figure 2A:
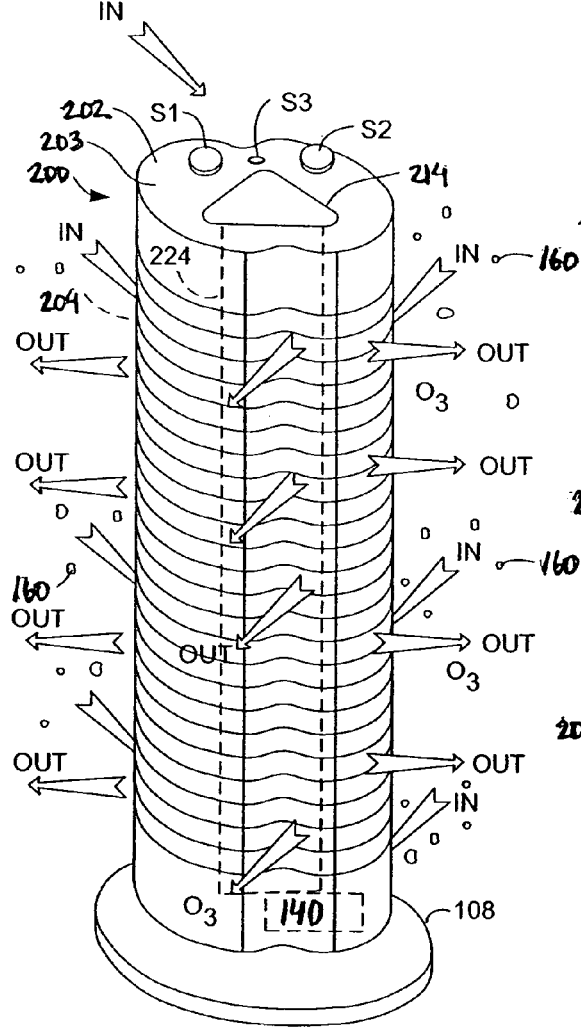
FIG. 2A is a perspective view of a housing for an air transporter-conditioner system, in accordance with one embodiment of the present invention.
Figure 2B:
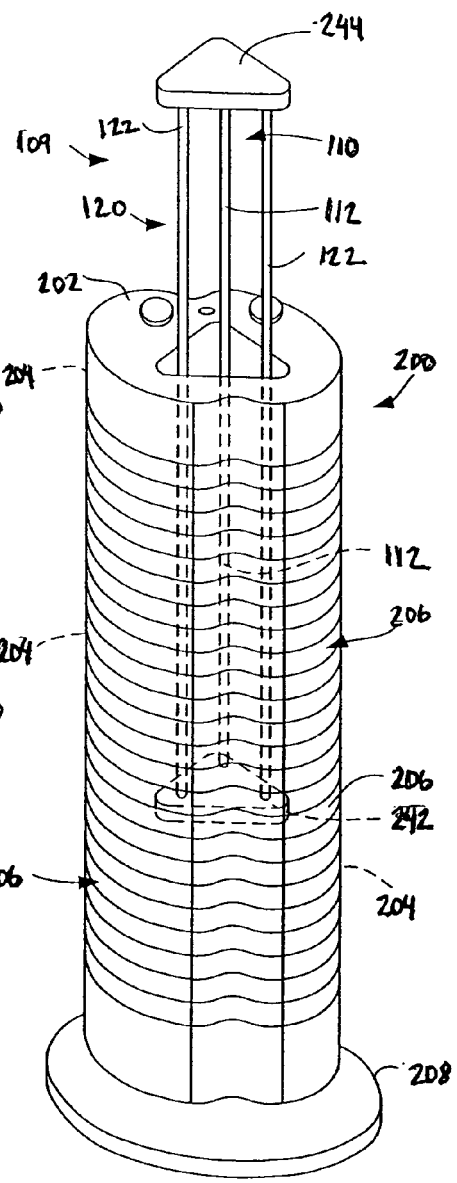
FIG. 2B is a perspective view of the housing shown in FIG. 2A illustrating removal of first and second electrode arrays connected with a single frame.
Figure 2C:
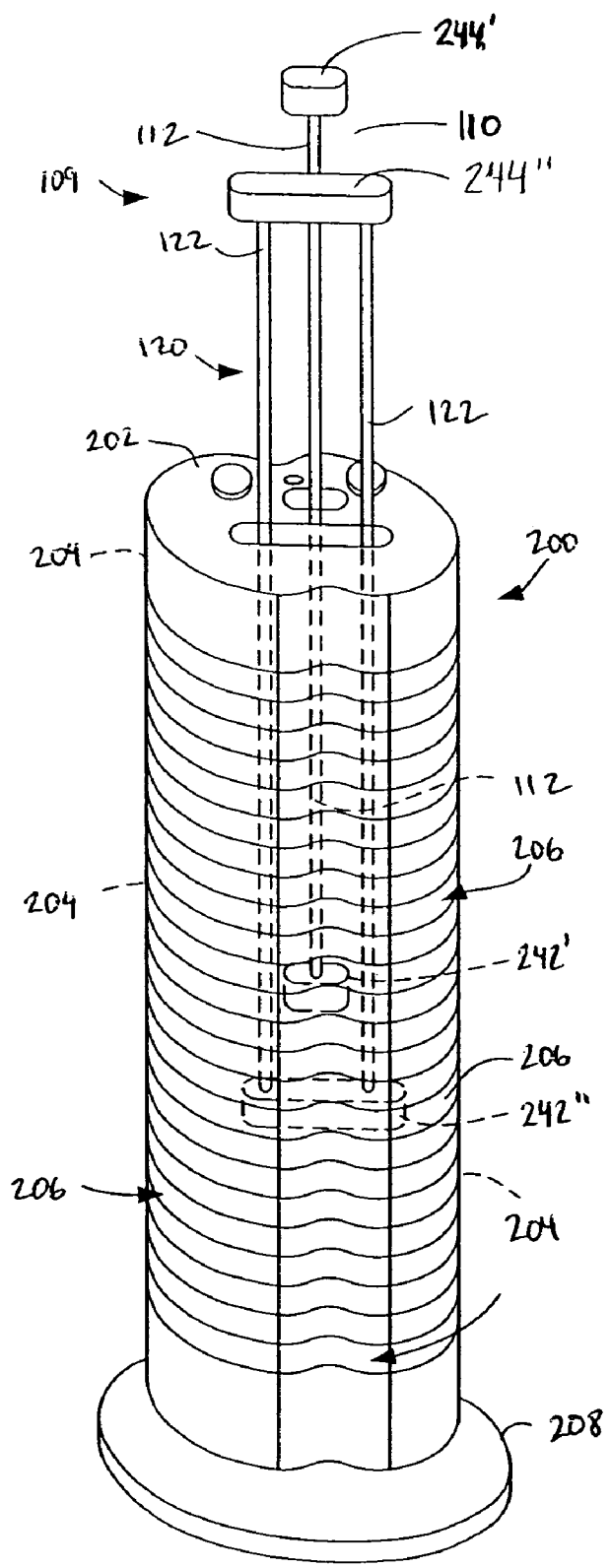
FIG. 2C is a perspective view of the housing of FIG. 2A illustrating removal of the first and second electrodes connected with separate frames.

Overall Air Transporter-Conditioner System Configuration:

FIGS. 2A-2C depict embodiments of an air transporter-conditioner system which do not have incorporated therein surfaces comprising a photocatalytic material, nor do the embodiments incorporate an activator for a photocatalytic material. However, these embodiments do include other aspects, such as removable second electrodes, which can be included in embodiments in accordance with the present invention described below.

FIGS. 2A-2C depict an electro-kinetic air transporter-conditioner system 200 whose housing 202 includes preferably rear-located intake vents or louvers 204 and preferably front located exhaust vents 206, and a base pedestal 208. If desired a single vent can provide and be used as both an air intake and an air exhaust with an air inlet channel and an air exhaust channel communicating with the vent and the electrodes. Preferably the housing is freestanding and/or upstandingly vertical and/or elongated. Internal to the transporter housing is an ion generating unit 140, preferably powered by an AC:DC power supply that is energizable or excitable using a switch S1 that can be conveniently located at the top 203 of the unit 200. The ion generating unit 140 is self-contained in that other than ambient air and external operating potential, nothing is required from beyond the transporter housing 202 for operation of the present invention.

The upper surface of the housing 202 includes a user-liftable handle member 244 which is used to remove an electrode assembly 109 from the housing 202 for the purpose of cleaning the electrode assembly 109. In the embodiment shown, the electrode assembly 109 includes a first array 110 of emitter electrodes 112 and a second array 120 of collector electrodes 122. The lifting member 244 can lift both the first array electrodes 110 and the second array electrodes 120 upward, causing the electrodes to telescope out of the top of the housing and, if desired, out of the unit 100 for cleaning. As shown in FIG. 2B, the electrode assembly 109 can be lifted vertically out from the top 203 of the unit 200 along the longitudinal axis or direction of the elongated housing 202. This arrangement makes it easy for the user to pull the electrodes out for cleaning. The bottom ends of the electrodes are connected to a member 242 such that the electrodes remain fixedly spaced and/or rigid. In other embodiments, the bottom ends of the electrodes need not be connected with a member 242. The first and second arrays of electrodes are coupled to the output terminals of the ion generating unit 140, as further discussed below.

In another embodiment, shown in FIG. 2C, a first array electrode 110 and second array electrodes 120 are each separately removable from the housing 202. In this embodiment, a first user-liftable handle member 244' can be used to remove the first array electrode 110 from the housing 202 and a second user-liftable handle member 244" can be used to remove second array electrodes 120 from the housing 202. The electrode arrays 110/120 can thus be separately cleaned which can prove advantageous, for example where the second array electrodes 120 require more frequent cleaning than the first array electrode 110. The first array electrode 110 can be left in the housing while the second array electrodes 120 are removed for cleaning, and vice versa. Further, the bottom end of the first array electrode 112 can be connected with a first lower support member 242', and the bottom ends of the second array electrodes 122 can be connected with a second lower support member 242". The lower support members can provide rigidity and maintain fixed spatial separation, and can further help protect the electrode arrays 110/120 from damage during frequent insertions and removals. In other embodiments the electrode arrays 110/120 need not be connected with lower support members.

In the exemplary embodiments shown in FIGS. 2A-2C, the first array 110 is shown as including a single electrode 112, and the second array 120 is shown as including two electrodes 122. However, in other embodiments, the first array 110 can include more than one electrode 112, and the second array 120 can include more than two electrodes 122, as will be shown in many of the remaining figures discussed below.

The general shape of the housing 202 shown in FIGS. 2A-2C is that of a figure eight in cross-section, although other shapes are within the spirit and scope of the invention. The top-to-bottom height of such a system can, for example, be about 1 m, the left-to-right width can be about 15 cm, and the front-to-back depth can be about 10 cm. Alternatively, myriad other dimensions and shapes can be used. A louvered construction provides ample inlet and outlet venting in an economical housing configuration. There need be no real distinction between vents 204 and 206, except their location relative to the second electrodes. These vents serve to ensure that an adequate flow of ambient air can be drawn into or made available to the system 200, and that an adequate flow of ionized air that includes appropriate amounts of $O_3$ flows out from system 200.

When the system 200 is energized using S1, high voltage or high potential output by ion generator 140 produces ions at the first electrode(s), which ions are attracted to the second electrodes. The movement of the ions in an "IN" to "OUT" direction carries with the ions air molecules, thus electro-kinetically producing an outflow of ionized air. The "IN" notation in FIGS. 2A-2C denote the intake of ambient air with particulate matter 160. The "OUT" notation denotes the outflow of cleaned air substantially devoid of the particulate matter, which particulate matter adheres electrostatically to the surface of the second electrodes. In the process of generating the ionized airflow appropriate amounts of ozone ($O_3$) are beneficially produced. It may be desired to provide the inner surface of the housing 202 with an electrostatic shield to reduce detectable electromagnetic radiation. For example, a metal shield could be disposed within the housing 202, or portions of the interior of the housing 202 can be coated with a metallic paint to reduce such radiation.

In one embodiment, the housing can be substantially oval-shaped or elliptically shaped in cross-section with dimpled side grooves. Thus, the cross-section can appear somewhat like a figure eight. It is within the scope of the present invention for the housing to have a different shaped cross-section such as, but not limited to, a rectangular shape, an egg shape, a tear-drop shape, or circular shape. The housing preferably has a tall, thin configuration. As will become apparent later, the housing is preferably functionally shaped to contain the electrode assembly.

As mentioned above, the housing has an inlet and an outlet. Both the inlet and the outlet are covered by fins or louvers. Each fin is a thin ridge spaced-apart from the next fin, so that each fin creates minimal resistance as air flows through the housing. The fins are horizontal and are directed across the elongated vertical upstanding housing of the unit. Thus, the fins are substantially perpendicular in this preferred embodiment to the electrodes. The inlet and outlet fins are aligned to give the unit a "see through" appearance. Thus, a user can "see through" the unit from the inlet to the outlet. The user will see no moving parts within the housing, but just a quiet unit that cleans the air passing therethrough. Alternatively the fins can be parallel with the electrodes in another preferred embodiment. Other orientations of fins and electrodes are possible in other embodiments.

Use of Air Transporter—Conditioner System to Remove VOCs and Odors from Air

Photocatalysis is a technique for removing pollutants from an air stream using a catalyst and ultraviolet (UV) irradiation of the catalyst to breakdown or oxidize hazardous chemicals such as VOCs. For example, one such catalyst is microporous titania ceramic (titanium dioxide, $TiO_2$), a thin layer of which can be coated on a surface to be placed in an air stream. Titanium dioxide is a semi-conducting photocatalyst having a band gap energy of 3.2 eV. When titanium dioxide is irradiated with photons having wavelengths of less than 385 nm, the band gap energy is exceeded and an electron is promoted from the valence band to the conduction band. The resultant electron-hole pair has a lifetime that enables its participation in chemical reactions. A UV light source (or a source of radiation outside of the UV spectrum having a wavelength less than 385 nm) can be used to activate the titania ceramic, which when illuminated can oxidize VOCs present in the air stream, breaking the compounds into water and carbon dioxide. In addition, irradiating an airflow with UV light can substantially eliminate microorganisms within the airflow.

In several embodiments of electrode assemblies described herein, interstitial or driver electrode(s) can include a photocatalytic coating, or can be embedded or impregnated with photocatalytic material. Use of a photocatalytic coating can promote oxidation of air in close proximity to the interstitial or driver electrode array. In other embodiments, the walls of a housing of the system can be embedded or impregnated with photocatalytic material, or the walls of the housing can include a photocatalytic coating, while in still other embodiments a porous structure, such as a separate mesh or grid, at least partially coated or embedded with a photocatalytic material can be positioned in the airflow adjacent to a UV light source. The porous structure need not have a grid-like structure. For example, the porous structure can have a web-like structure, or a spiral structure. Further, in some other embodiments, where an airflow already exists (for example in a furnace duct), the porous structure can be placed within the airflow (for example disposed within the furnace duct) rather than within an airflow generated by an electrode assembly. A UV light source can be positioned such that the porous surface is irradiated by UV light. There are myriad different ways of introducing photocatalytic material to the airflow.

Various types of catalysts can be used in a photocatalytic coating. For example, as described above the photocatalytic coating can be comprised of titania ceramic. In other embodiments, the photocatalytic coating can be comprised of an alternative metal oxide, such as zinc oxide, cuprous oxide, silicon dioxide, etc. Oxides of manganese, copper, cobalt, chromium, iron and nickel are known to be active in oxidation reactions. Further, mixed oxides can be used for photocatalysis. For example, in some circumstances copper chromite ($CuCrO_4$) can be at least as active in promoting oxidation as cuprous oxide (CuO). These are just examples of coatings that can be used with embodiments of the present invention. Still further, noble metals can be effectively used to oxidize VOCs. For example, oxidation reactions on platinum and palladium are known to occur very rapidly. In some embodiments, a noble metal can be impregnated or applied to a surface as a coating, for example with another substance (the amount of platinum and palladium is dependent on the level of VOCs present, but effectively a fraction of a percent relative to a total surface area on which it is applied). Oxidation of VOCs using a base metal photocatalytic coating may produce carbon monoxide (CO) as an oxidation byproduct. In one embodiment of the present invention, a noble metal, such as platinum or palladium, can be deposited, impregnated or otherwise applied to the base metal photocatalytic coating, or a surface or porous structure including the base metal photocatalyst. It is known in the art that platinized titania ceramic, for example, can enhance the further oxidation of CO. One of ordinary skill in the art will appreciate that other types of photocatalytic materials are also within the spirit and scope of the present invention.

FIGS. 3A-6 illustrate embodiments in accordance with the present invention of an electro-kinetic air transporter-conditioner system having an improved ability to diminish or destroy microorganisms including bacteria, germs, and viruses in an airflow, and an improved ability to reduce VOCs in the airflow. Specifically, FIGS. 3A-6 illustrate various preferred embodiments of the elongated and upstanding housing 302 with the operating controls located on the top surface 303 of the housing 302 for controlling the system 300.

Figure 3A:
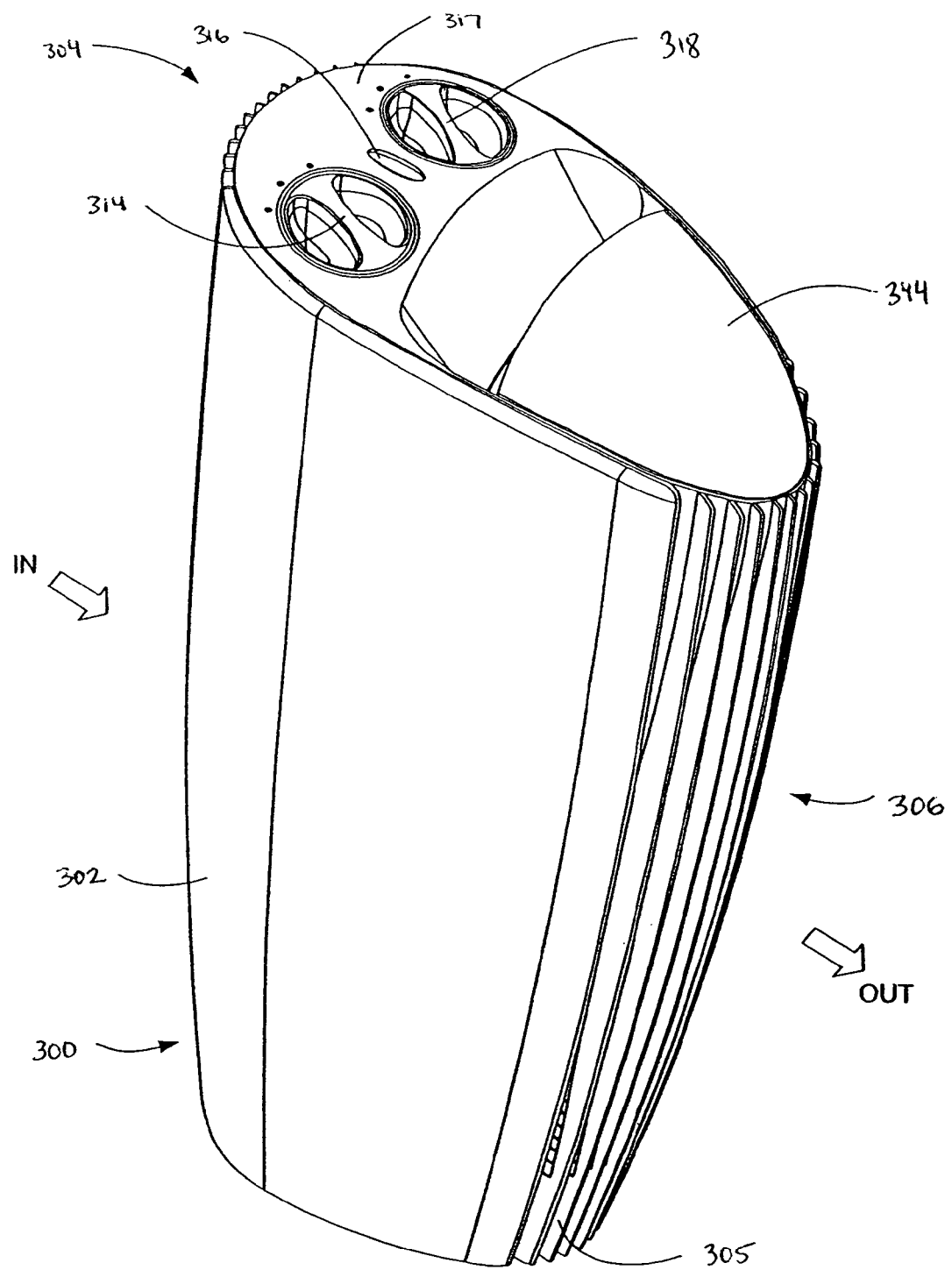
FIG. 3A is a perspective view of an alternative embodiment of a housing for use with a system in accordance with the present invention without a base.

FIG. 3A is a perspective view of a housing 302 for use with a system in accordance with one embodiment of the present invention. The housing 302 can be made from a lightweight, inexpensive material capable of withstanding prolonged exposures to class UV-C light resulting from use of a UV light located within the housing 302 (described hereinafter). Non-"hardened" material can degenerate over time if exposed to light such as UV-C, and can therefore be inappropriate for use. By way of example only, the housing 302 can be manufactured from CYCLOLAC® ABS Resin (material designation VW300(f2)) which is manufactured by General Electric Plastics Global Products and certified by Underwriters Laboratory (UL) Inc. for use with UV light. It is within the scope of the present invention to manufacture the housing 302 from other UV appropriate materials.

In one embodiment, the housing 302 can be one of oval, elliptical, teardrop and egg-shaped. The housing 302 can include at least one air inlet 304, and at least one air outlet 304. As used herein, it will be understood that the inlet 304 is "upstream" relative to the outlet 304, and that the outlet 304 is "downstream" from the inlet 304. "Upstream" and "downstream" describe the general flow of air into, through, and out of the system 300, as indicated by the large hollow arrows.

Covering the inlet 304 and the outlet 306 are fins, louvers, or baffles 305. The fins 305 are preferably elongated and upstanding, and thus vertically oriented to minimize resistance to the airflow entering and exiting the system 300. Preferably the fins 305 are oriented approximately parallel to at least the second collector electrode array 120. The fins 305 can also be parallel to the first emitter electrode array 110. This configuration assists in the flow of air through the system 300 and can prevent UV light from a UV lamp, or other photocatalytic activator, from exiting the housing 302. By way of example only, if the long width of the body from the inlet 304 to the outlet 306 is eight inches, the collector electrode 122 (shown in FIG. 5A) can be 1¼" wide in the direction of airflow, and the fins 305 can be ¾" or ½" wide in the direction of airflow. Of course, other dimensions are within the spirit and scope of the invention. Further, other fin and housing shapes which are not as aerodynamic are within the spirit and scope of the invention.

The cross-section of the housing 302 can be one of oval, elliptical, teardrop and egg-shaped so that the inlet 304 and outlet 306 are narrower than the body of the housing. Accordingly as the airflow passes, for example across line A-A shown in FIG. 5A, the airflow is slowed due to the increased width and cross-sectional area of the housing 302. Microorganisms and VOCs within the airflow thus have a greater dwell time, allowing microorganisms to be killed by the UV lamp acting as a germicidal device, and VOCs to react and oxidize in the presence of photocatalytic material activated by the UV lamp operating as an activator.

Figure 3B:
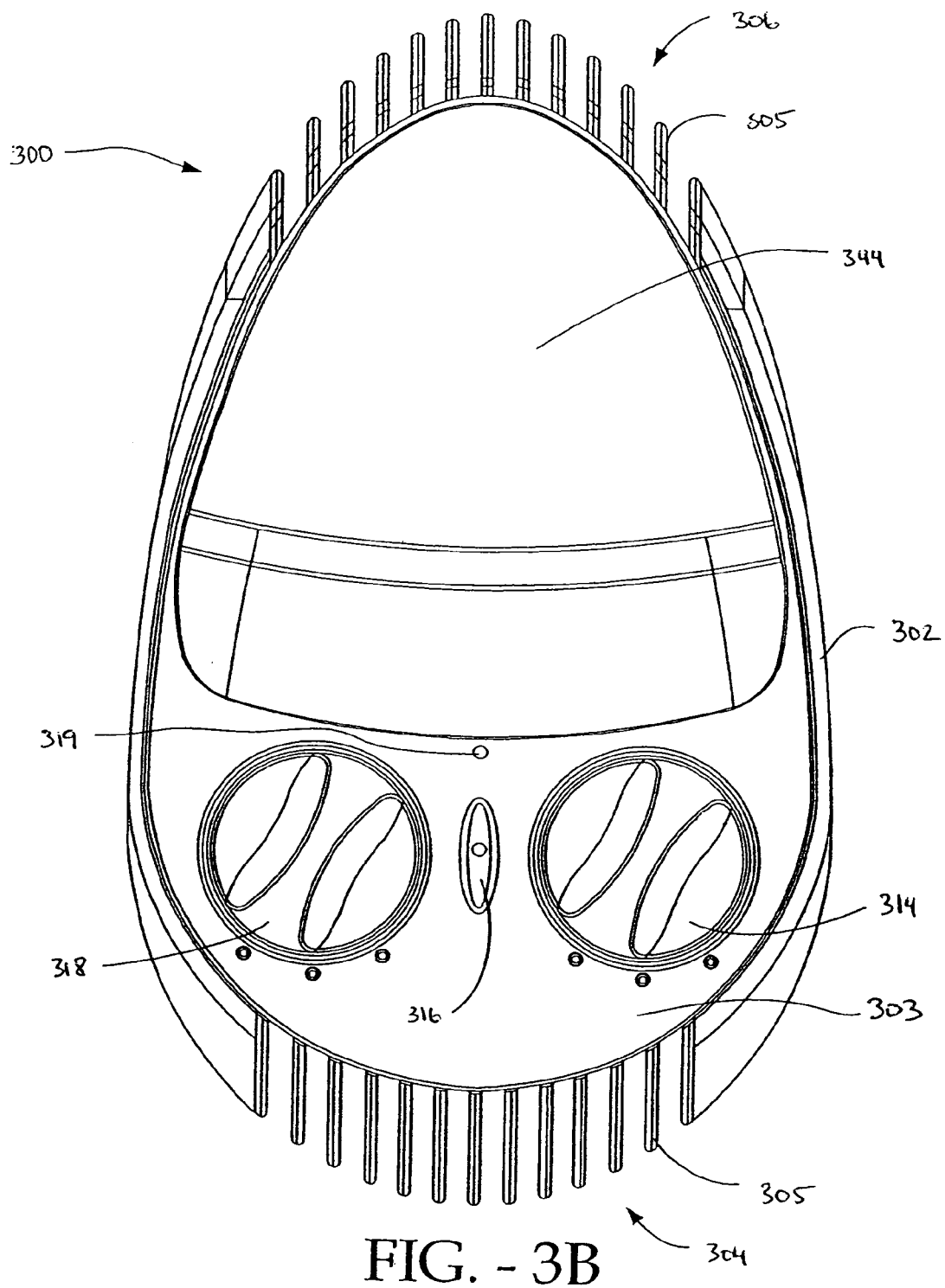
FIG. 3B is a top view of the housing of FIG. 3A.

FIG. 3B illustrates the operating controls for the system 300. Located on a top surface 303 of the housing 302 is an airflow speed control dial 314, a boost button 316, a function dial 318, and an overload/cleaning light 319. The airflow speed control dial 314 has three settings from which a user can choose: LOW, MED, and HIGH. The airflow rate is proportional to the voltage differential between the electrodes or electrode arrays coupled to the ion generator 140. The LOW, MED, and HIGH settings generate a different predetermined voltage difference between the first and second arrays. For example, the LOW setting will create the smallest voltage difference, while the HIGH setting will create the largest voltage difference. Thus, the LOW setting will cause the system 300 to generate the slowest airflow rate, while the HIGH setting will cause the system 300 to generate the fastest airflow rate. These airflow rates are created by the electronic circuit shown schematically in FIGS. 9A and 9B, and operate as disclosed below.

The function dial 318 enables a user to select "ON," "ON/GP," or "OFF." The unit 300 functions as an electrostatic air transporter-conditioner, creating an airflow from the inlet 304 to the outlet 306, and removing particles from the airflow when the function dial 318 is set to the "ON" setting or the "ON/GP" setting. The UV lamp does not operate, or emit light, when the function dial 318 is set to "ON." Setting the function dial 318 to "ON/GP" activates the UV lamp 390, which emits UV light, killing microorganisms within the airflow and irradiating a photocatalytic material. The photocatalytic material is activated when irradiated and reacts with VOCs in the airflow. The system 300 does not operate when the function dial 318 is set to the "OFF" setting.

In some embodiments, the system 300 can further generate small amounts of ozone to reduce odors within a room. Where the odors are caused by VOCs (as described above) activation of the UV lamp can further reduce the odors. If there is an extremely strong odor within the room, or a user would like to temporarily accelerate the rate of cleaning, the system 300 can have a boost button 316. When the boost button 316 is depressed, the system 300 will temporarily increase the airflow rate to a predetermined maximum rate, and generate an increased amount of ozone. The increased amount of ozone can reduce the odor in the room faster than if the system 300 is set to HIGH. The maximum airflow rate will also increase the particle capture rate of the system 300. In a preferred embodiment, pressing the boost button 316 will increase the airflow rate and ozone production continuously for 5 minutes. This time period may be longer or shorter. At the end of the preset time period (e.g., 5 minutes), the system 300 will return to the airflow rate previously selected by the control dial 314.

An overload/cleaning light 319 can indicate if the second electrodes 122 require cleaning, or if arcing occurs between the first and second electrode arrays. In some embodiments, the overload/cleaning light 319 can illuminate either amber or red in color. The light 319 will turn amber if the system 300 has been operating continuously for more than two weeks and the second array 120 has not been removed for cleaning within the two week period. The amber light is controlled by the below described 2-week time circuit 930 (see FIG. 9B) which is connected to the power setting circuit 922. The system 300 will continue to operate after the light 319 turns amber. The light 319 is only an indicator. There are two ways to reset or turn the light 319 off: a user can remove and replace the second array 120 from the unit 300, and/or the user can turn the control dial 318 to the OFF position, and subsequently turn the control dial 318 back to the "ON" or "ON/GP" position. The timer circuit 930 will reset and begin counting a new two week period upon completing either of these two steps.

The light 319 will turn red to indicate that arcing has occurred between the first array 110 and the second array 120, as sensed by a sensing circuit 932, which is connected between the IGBT switch 926 and the connector oscillator 924 of FIG. 9B (as described below). When arcing occurs, the system 300 will automatically shut itself off. The system 300 cannot be restarted until the system 300 is reset. To reset the system 300, the second array 120 should first be removed from the housing 302 after the system 300 is turned off. The second electrode 120 can then be cleaned and placed back into the housing 302. The system 300 can then be turned on. If no arcing occurs, the system 300 will operate and generate an airflow. If the arcing between the electrodes continues, the system 300 will again shut itself off and must be reset.

Figure 3C:
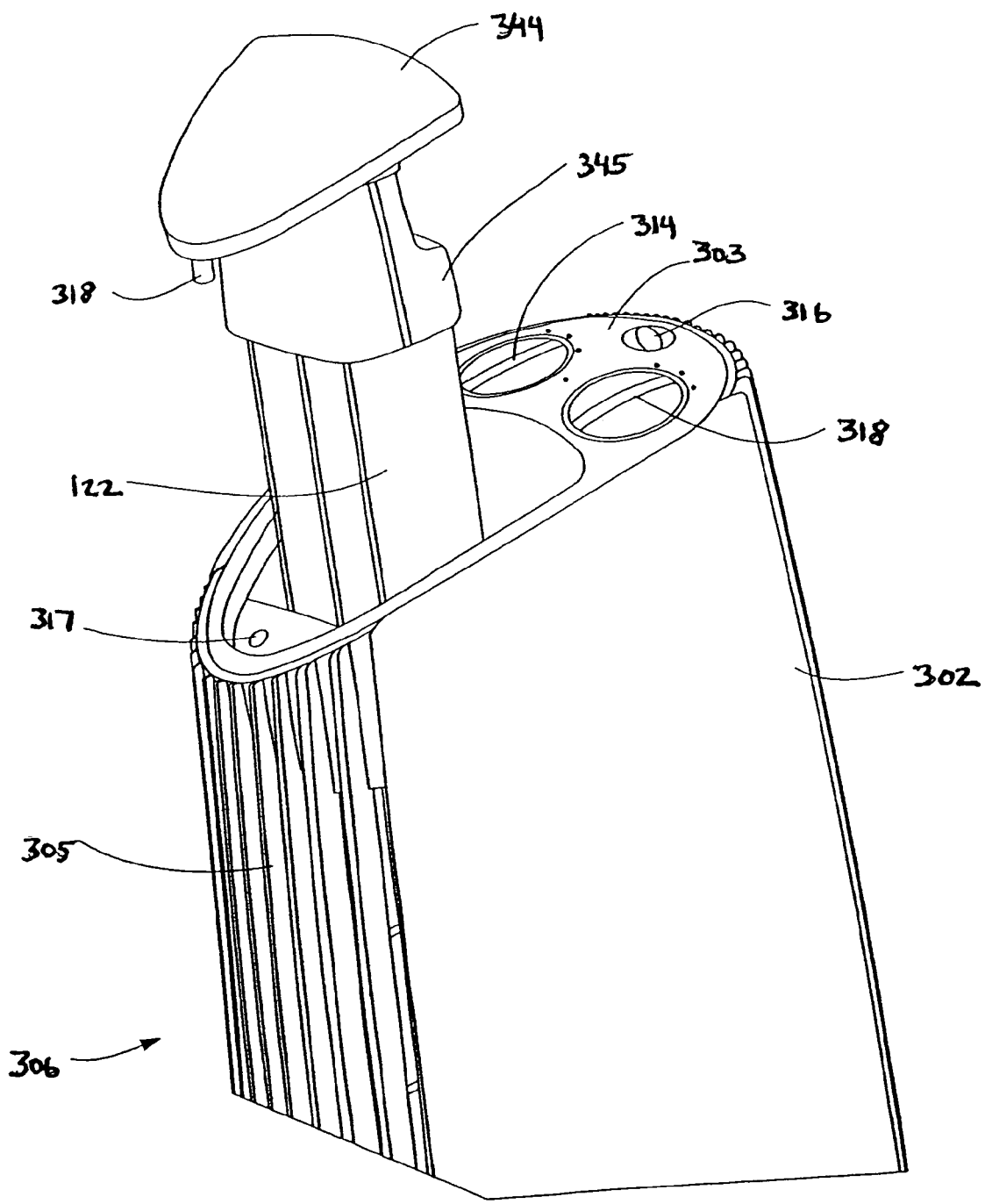
FIG. 3C is a partial perspective view of the housing of FIGS. 3A and 3B, illustrating a removable second electrode array.

FIG. 3C illustrates the second electrodes 122 partially removed from the housing 302. In this embodiment, a handle 344 is attached to an electrode mounting bracket 345. The bracket 345 secures the second electrodes 122 in a fixed, parallel configuration. Another similar bracket 345 can be attached to the second electrodes 122 substantially at the bottom (not shown). The two brackets 345 align the second electrodes 122 parallel to each other, and in-line with the airflow traveling through the housing 302. Preferably, the brackets 345 are non-conductive surfaces.

An interlock post 318 extends from the bottom of the handle 344. When the second electrodes 122 are placed completely into the housing 302, the handle 344 rests within the top surface 303 of the housing. In this position, the interlock post 318 protrudes into the interlock recess 317 and activates a switch connecting the electrical circuit of the unit 300. When the handle 344 is removed from the housing 302, the interlock post 318 is pulled out of the interlock recess 317 and the switch opens the electrical circuit. With the switch in an open position, the unit 300 will not operate. Thus, if the second electrodes 122 are removed from the housing 302 while the system 300 is operating, the system 300 will shut off as soon as the interlock post 318 is removed from the interlock recess 317.

Figure 3D:
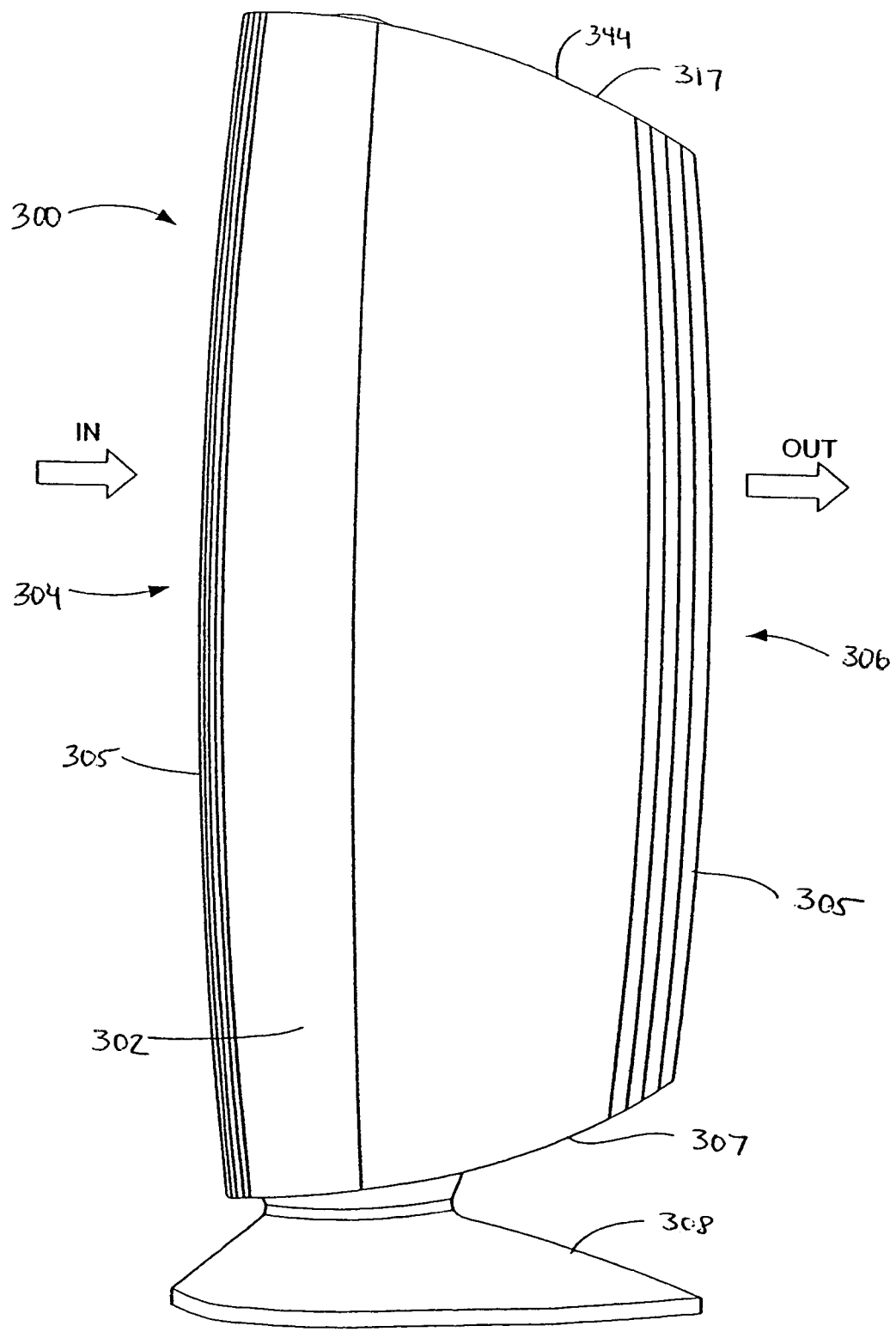
FIG. 3D is a side view of the housing of FIG. 3A including a base.

FIG. 3D illustrates the housing 302 as mounted on a stand or base 308. The housing 302 has an inlet 304 and an outlet 304. The base 308 sits on a floor surface. The base 308 allows the housing 302 to remain in a vertical position. It is within the scope of the present invention for the housing 302 to be pivotally connected to the base 308. The housing 302 includes a sloped top surface 303 and a sloped bottom surface 307. These surfaces slope inwardly from inlet 304 to outlet 304 to additionally provide a streamline appearance and effect.

Figure 3E:
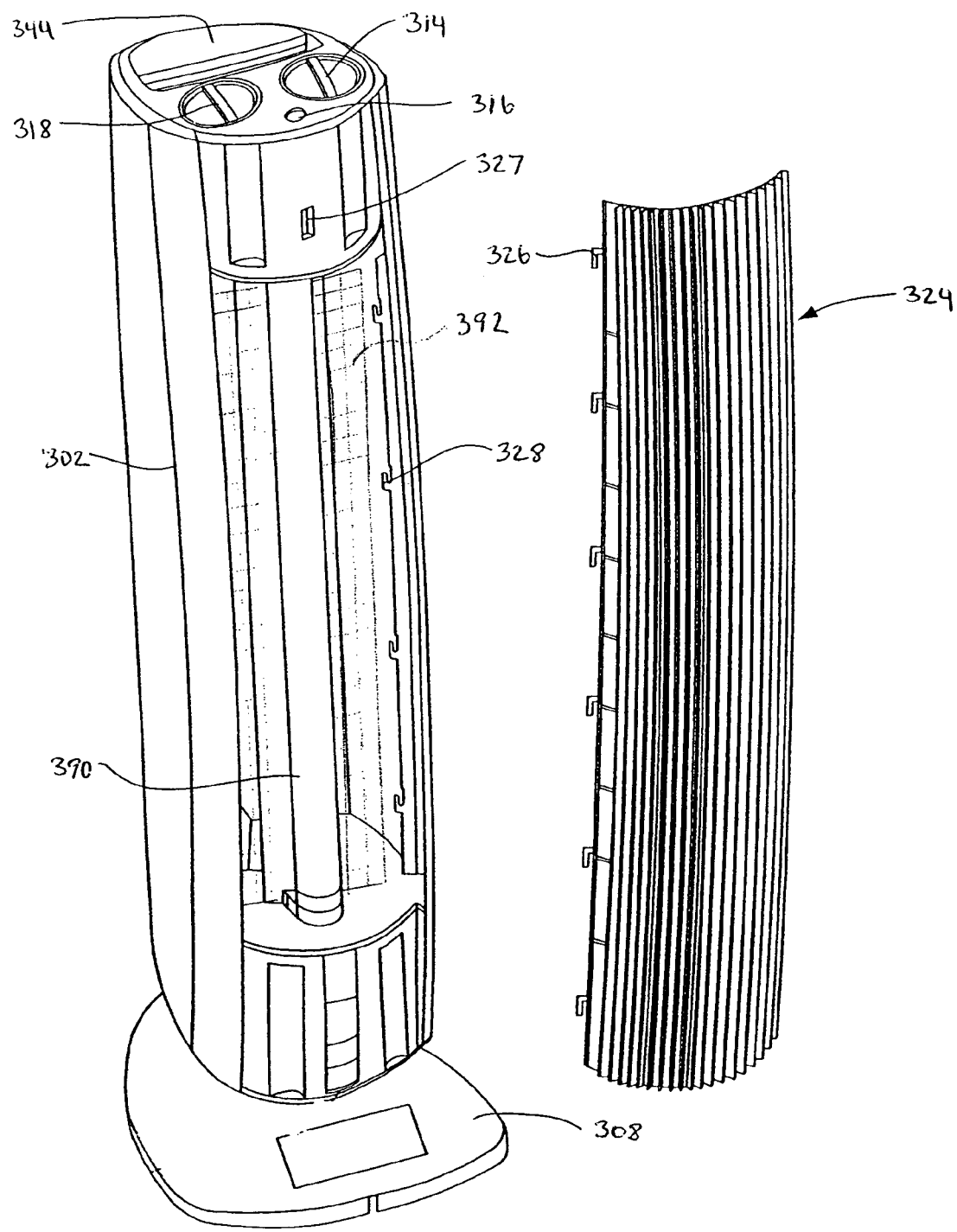
FIG. 3E is a perspective view of the housing of FIG. 3D, illustrating removal of a rear panel (an inlet panel)

FIG. 3E illustrates the housing 302 having a removable rear panel 324, allowing a user to easily access and remove the UV lamp 390, for example when the UV lamp 390 expires. Optionally, removal of the rear panel 324 can allow access to a mesh or grid 392 having a coating of photocatalytic material and positioned adjacent to the UV lamp 390 and within the airflow so that the grid 392 can be removed from the housing 302, for example when the grid 392 requires re-coating or regeneration (for example by baking at high temperature). In industrial applications, modern base metal oxide photocatalysts are known to operate for five to six years without a decrease in performance. The rear panel 324 in this embodiment defines the air inlet and comprises vertical louvers. The rear panel 324 has locking tabs 326 located on each side, along the entire length of the panel 324. The locking tabs 326 as shown are "L"-shaped. Each tab 324 extends away from the panel 324, inward towards the housing 302, and then projects downward, parallel with the edge of the panel 324. It is within the spirit and scope of the invention to alternatively include tabs 326 having a different shape. Each tab 326 individually and slidably interlocks with recesses 328 formed within the housing 302. The rear panel 324 also has a biased lever (not shown) located at the bottom of the panel 324 that interlocks with the recess 230. To remove the panel 324 from the housing 302, the lever is urged away from the housing 302, and the panel 324 is slid vertically upward until the tabs 326 disengage the recesses 328. The panel 324 is then pulled away from the housing 302.

The panel 324 can include a safety mechanism to shut the system 300 off when the panel 324 is removed, or render the system 300 inoperable. The panel 324 has a rear projecting tab (not shown) that engages a safety interlock recess 327 when the panel 324 is secured to the housing 302. By way of example only, the rear tab depresses a safety switch located within the recess 327 when the rear panel 324 is secured to the housing 302. The system 300 will operate only when the rear tab in the panel 324 is fully inserted into the safety interlock recess 327. When the panel 324 is removed from the housing 302, the rear projecting tab is removed from the recess 327 and the power is cut-off to the entire system 300. For example if a user removes the rear panel 324 while the system 300 is running, and the UV lamp 390 is emitting UV light, the system 300 will turn off as soon as the rear projecting tab disengages from the recess 327. Preferably, the system 300 will turn off when the rear panel 324 is removed only a very short distance (e.g., ¼") from the housing 302. This safety switch operates very similar to the interlocking post 318.

Figure 4:
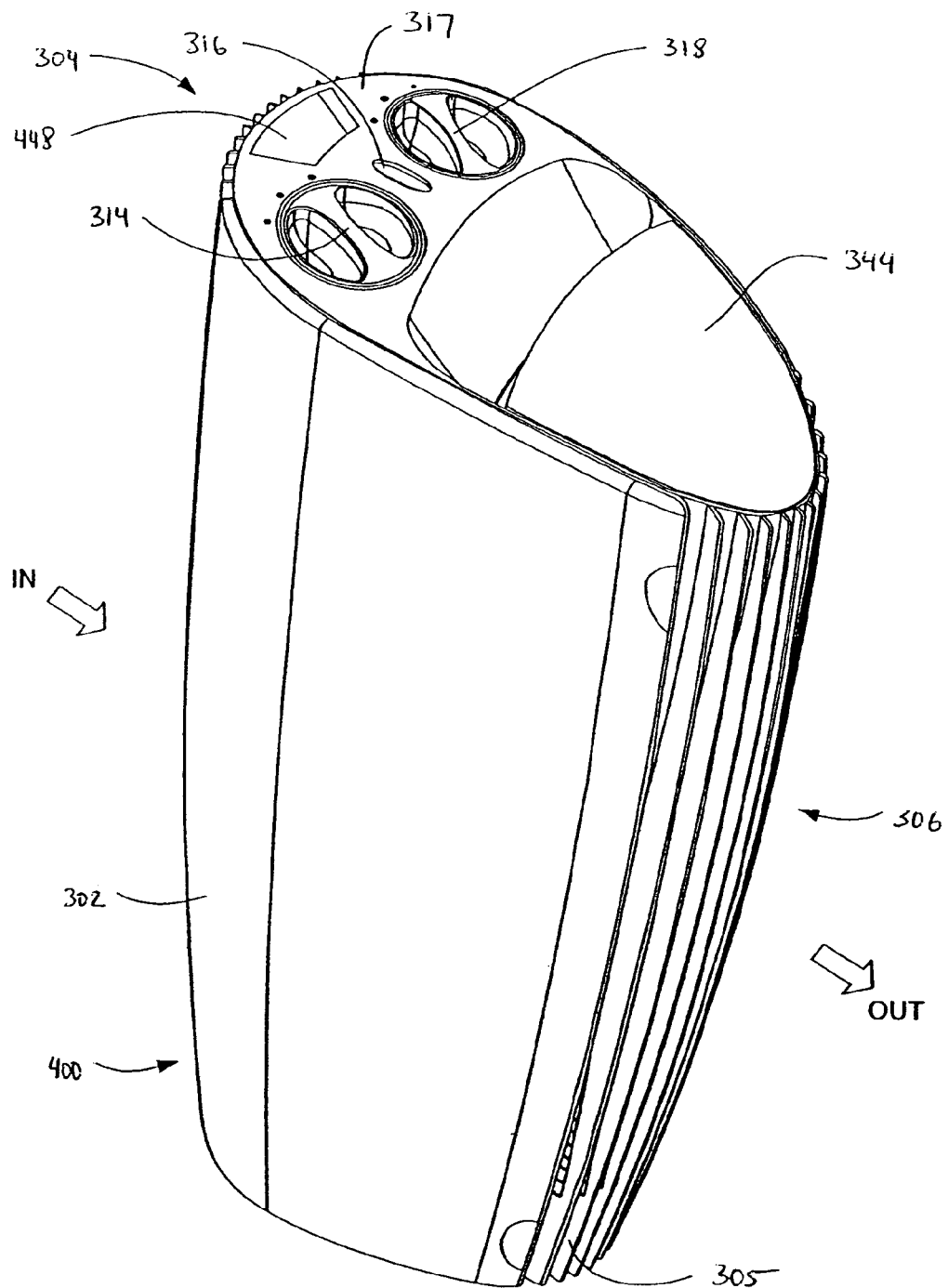
FIG. 4 is a perspective view of still another embodiment of the housing having a handle for vertical removal of a UV lamp from the housing.

FIG. 4 illustrates yet another embodiment of the housing 302. In this embodiment, the UV lamp 390 can be removed from the housing 302 by lifting the UV lamp 390 out of the housing 302 through the top surface 303. The housing 302 need not have are movable rear panel 324. Instead, a handle 448 is affixed to the UV lamp 390. The handle 448 can be recessed within the top surface 303 of the housing 302 when the UV lamp 390 is within the housing 302. To remove the UV lamp 390, the handle 448 is vertically raised out of the housing 302.

The UV lamp 390 can be situated within the housing 302 in a similar manner as the second array of electrodes 120, such that when the UV lamp 390 is pulled vertically out of the top 303 of the housing 302 the electrical circuit providing power to the UV lamp 390 is disconnected. The UV lamp 390 can be mounted in a fixture having circuit contacts which engage the circuit of FIG. 9A. If the UV lamp 390 and fixture are pulled out, the circuit contacts are disengaged. Further, as the handle 448 is lifted from the housing 302, a cutoff switch will shut the system 400 off. This safety mechanism ensures that the system 400 will not operate without the UV lamp 390 placed securely in the housing 302, preventing an individual from directly viewing UV light emitted from the UV lamp 390. Reinserting the UV lamp 390 into the housing 302 causes the fixture to re-engage the circuit contacts. In similar, but less convenient fashion, the UV lamp 390 can be designed to be removed from the bottom of the housing 302.

The UV lamp 390 is preferably a UV-C lamp that emits light and radiation (in combination referred to as UV radiation or UV light) having a wavelength of about 254 nm. This wavelength is effective in diminishing or destroying bacteria, germs, and viruses to which it is exposed, and effective in activating the photocatalytic material coating at least a portion of the grid 392, or alternatively, coating portions of interstitial electrodes or a portion of an inner surface of the housing. For example, the UV lamp 390 can be a Phillips model TUV 15W/G15T8, a 15 W tubular lamp measuring about 25 mm in diameter by about 43 cm in length. Another suitable UV lamp is the Phillips TUV 8WG8 T6, an 8 W lamp measuring about 15 mm in diameter by about 29 cm in length. Other UV lamps that emit the desired wavelength can instead be used.

Figure 5A:
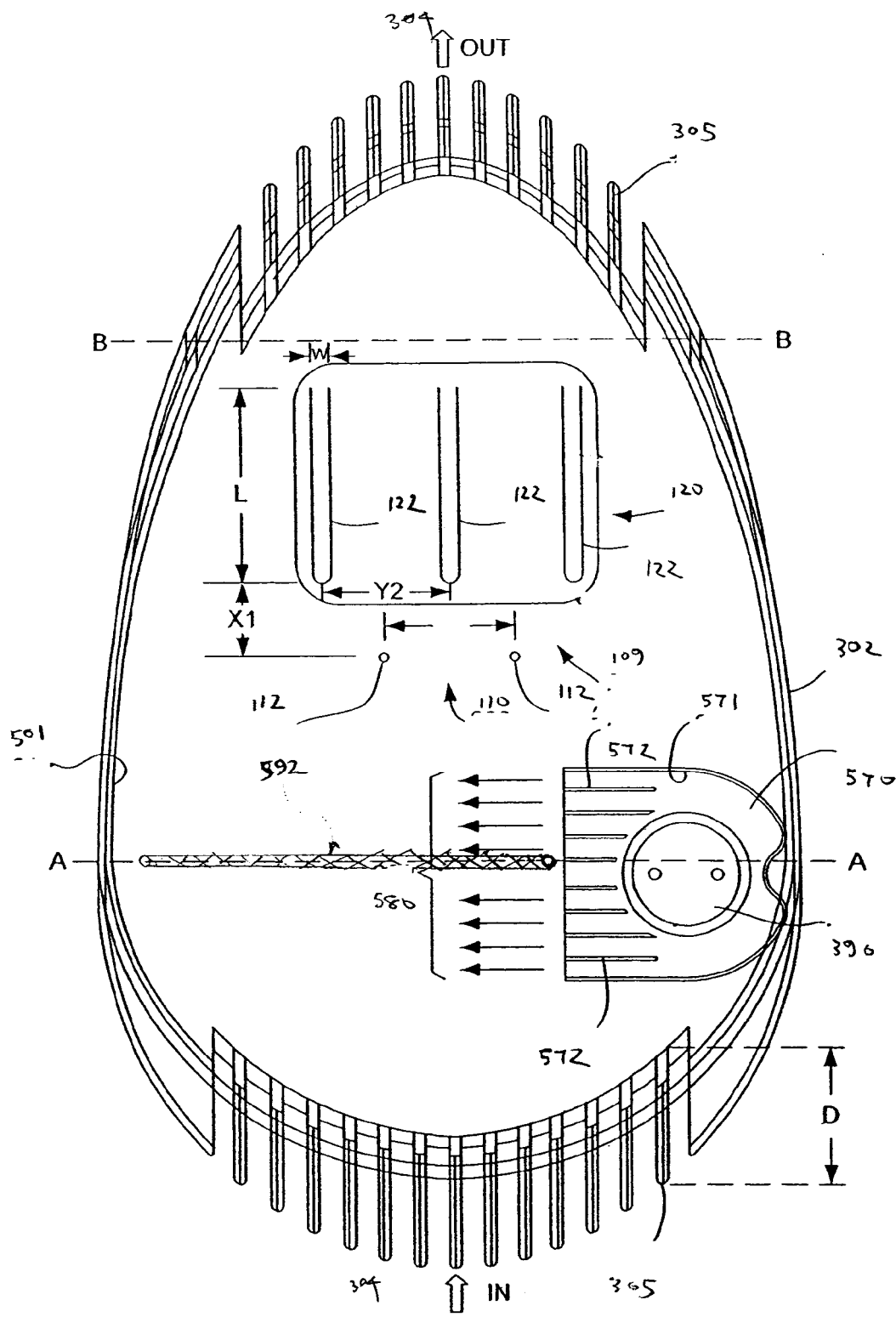
FIG. 5A is a cross-sectional view of an air transporter-conditioner system in accordance with one embodiment of the present invention, including a UV lamp and grid.
Figure 5B:
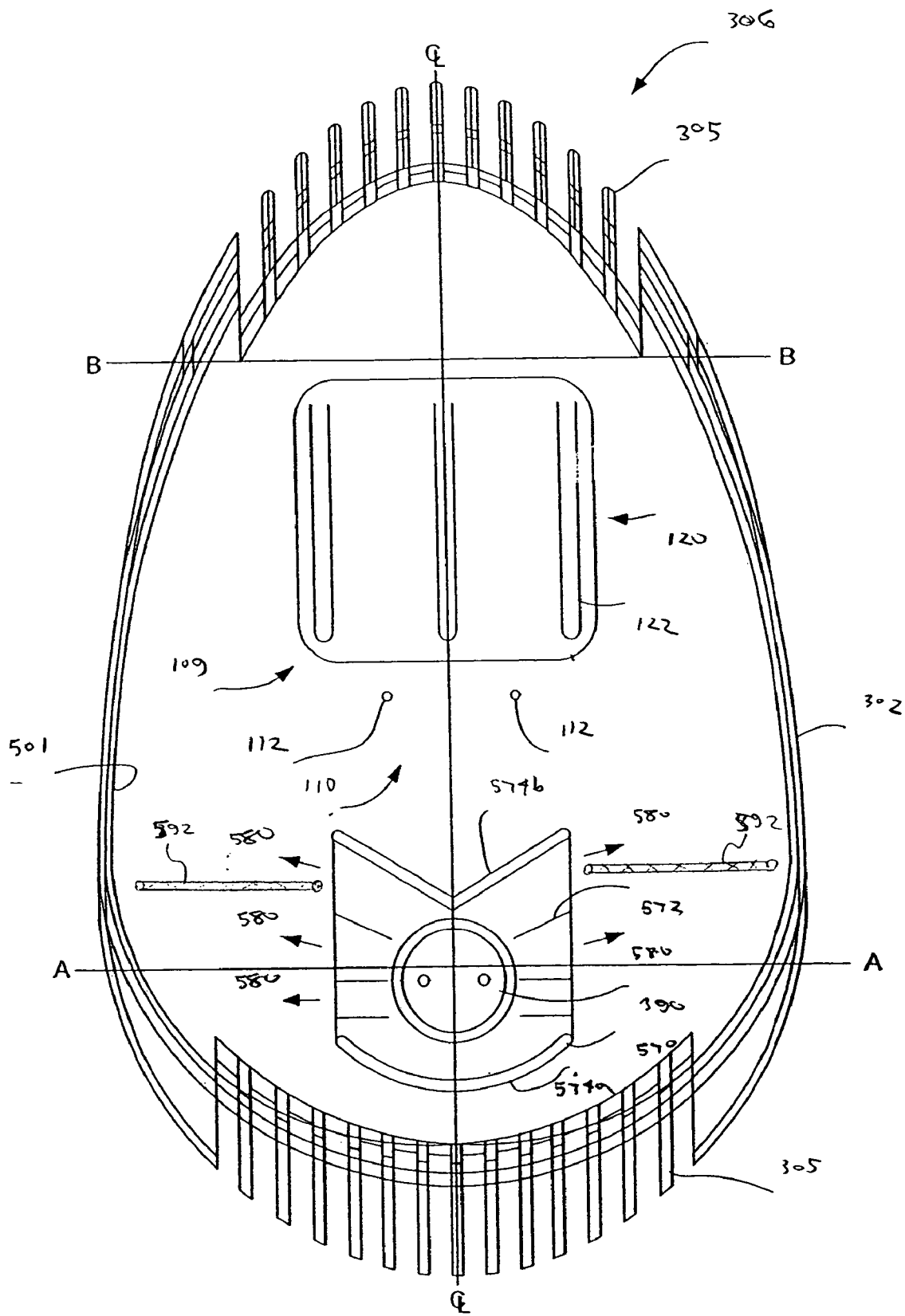
FIG. 5B is a cross-sectional view of an air transporter-conditioner system in accordance with an alternative embodiment of the present invention.

As previously mentioned, the housing 302 prevents an individual from viewing U light generated by a UV lamp 390 disposed within the housing 302. FIGS. 5A and 5B illustrate preferred locations of the UV lamp 390 within the housing 302, and further show the spacial relationship between the UV lamp 390 and electrode assembly 109, and the UV lamp 390 and the inlet 304, the outlet 306, and the inlet and outlet louvers.

In one embodiment, an inner surface 501 of the housing 302 diffuses or absorbs UV light emitted from the UV lamp 390. The UV lamp 390 can emit some UV light 580 directly onto the inner surface 501 of the housing 302. By way of example only, the inner surface 501 of the housing 302 can be formed with a non-smooth finish, or a non-light reflecting finish or color, thus absorbing or disbursing the UV light and preventing the UV light from exiting through either the inlet 304 or the outlet 306.

As discussed above, the fins 305 covering the inlet 304 and the outlet 306 also limit any line of sight of the user into the housing 302. The fins 305 are vertically oriented within the inlet 304 and the outlet 306. The depth D of each fin 305 is preferably deep enough to prevent an individual from directly viewing the inner surface 501. In one embodiment, the inner surface 501 cannot be directly viewed by moving from side-to-side, while looking into the outlet 306 or the inlet 304. Looking between the fins 305 and into the housing 302 allows an individual to "see through" the system 500. That is, a user can look into the inlet vent 304 or the outlet vent 306 and see out of the other vent. It is to be understood that it is acceptable to see light or a glow coming from within the housing 302, if the light has a non-UV wavelength that is acceptable for viewing. In general, when UV light 580 strikes the interior surface 501 of the housing 302, the UV light 580 is shifted from its UV spectrum. The wavelength of the light changes from the UV spectrum into an appropriate viewable spectrum. Thus, any light emitted from within the housing 302 is appropriate to view.

Figure 6:
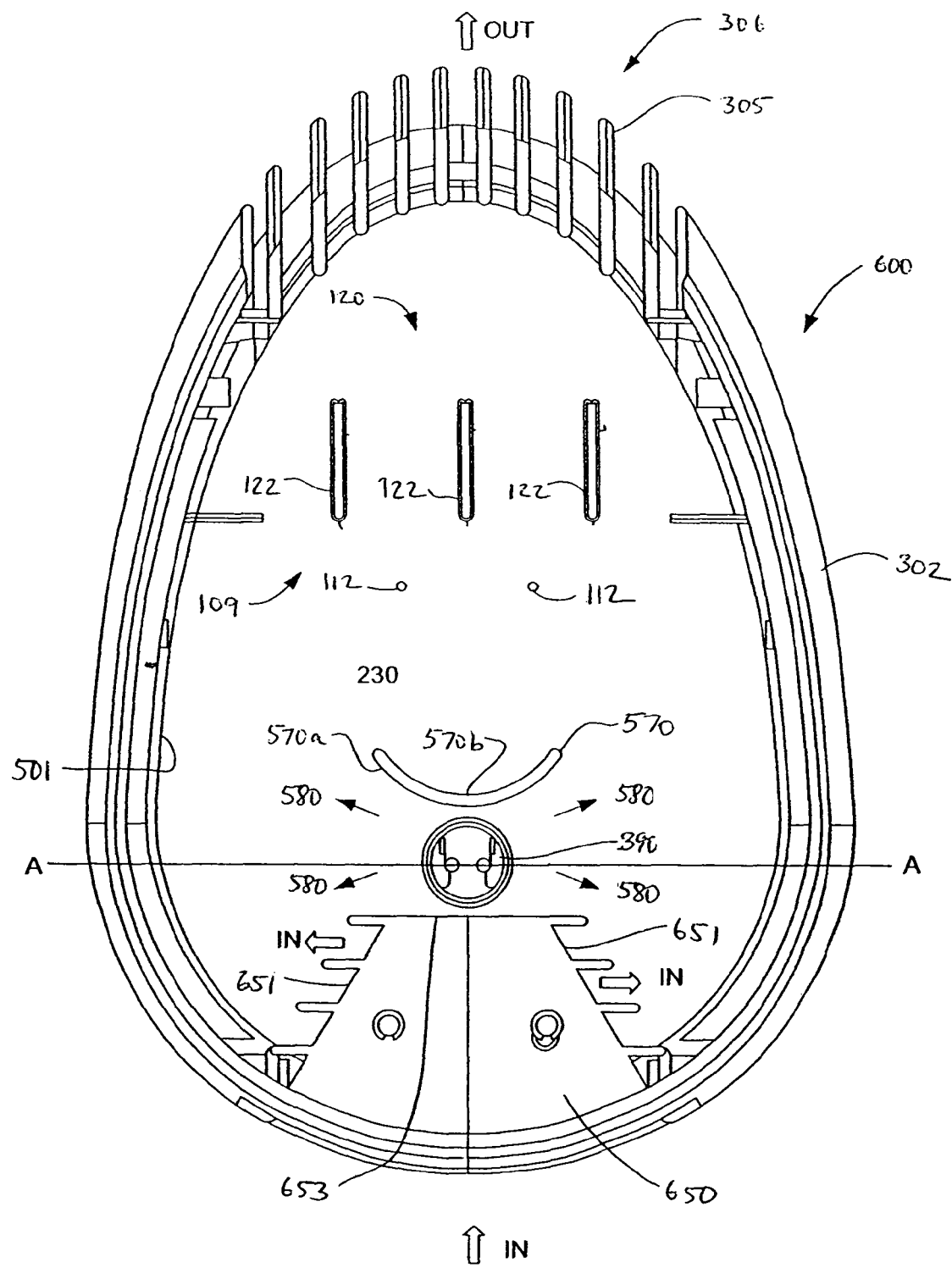
FIG. 6 is a cross-sectional view of an air transporter-conditioner system in accordance with still another embodiment of the present invention.

The housing 302 is designed to optimize the reduction of microorganisms and VOCs within the airflow. The efficacy of UV light 580 upon microorganisms can depend upon the length of time such organisms are subjected to the UV light 580. Thus, the UV lamp 390 can be located within the housing 302 where the airflow is the slowest. Likewise, the efficacy of a catalytic material on VOCs can depend upon the length of time such VOCs are given to react in the presence of catalytic material. As illustrated in FIG. 5A-6, in preferred embodiments, the UV lamp 390 is disposed within the housing 302 along line A-A. The housing 302 creates a fixed volume through which the air passes. Air enters the inlet 304 having a smaller width and cross-sectional area relative to the portion of the housing 302 along line A-A. Since the width and cross-sectional area of the housing 302 along line A-A are larger than the width and cross-sectional area of the inlet 304, the airflow will decelerate from the inlet 304 to the line A-A. By placing the V lamp 390 substantially along line A-A, the air will have the longest dwell time as it passes through the UV light 580 emitted by the UV lamp 390. Likewise, positioning the grid 392 approximately in a plane formed along the line A-A (or at a slight angle to the plane) can expose a substantial portion of the surface area of the grid 392 to the airflow and the UV light 580 emitted by the UV lamp 390, increasing the ability of the catalytic material coating the grid 392 to cause VOCs present in the airflow to breakdown (or oxidize). It is, however, within the scope of the present invention to locate the UV lamp 390 anywhere within the housing 302, preferably (but not exclusively) upstream of the electrode assembly 109. Likewise, the grid 392 can be positioned anywhere within the housing 302 such that the catalytic material is activated by the emission by the UV lamp 390. In other embodiments, the housing walls itself can be coated with photocatalytic material, or photocatalytic material can be embedded or impregnated into the inner surface of the housing 302.

A shell or housing 570 substantially surrounds the UV lamp 390. The shell 570 prevents UV light 580 from shining directly towards the inlet 304 or the outlet 304. In a preferred embodiment, the interior surface of the shell 570 that faces the UV lamp 390 is a non-reflective surface. By way of example only, the interior surface of the shell 570 can be a rough surface, or painted a dark, non-gloss color such as matte black. In some embodiments, the interior surface of the shell 570 can further be coated with a photocatalytic material in substitution of, or in addition to a grid 392 or a coated inner surface of the housing 302. The UV lamp 390, as shown in FIGS. 5A and 5B, is a circular tube parallel to the housing 302. In a preferred embodiment, the UV lamp 390 is substantially the same length as, or shorter than, the fins 305 covering the inlet 304 and outlet 304. The UV lamp 390 emits UV light 580 outward in a 360° pattern. The shell 570 blocks a portion of the UV light 580 emitted directly towards the inlet 304 and the outlet 304. As shown in FIGS. 5A and 5B, there is no direct line of sight through the inlet 304 or the outlet 304 that would allow a person to view the UV lamp 390. Alternatively, the shell 570 can have an internal reflective surface in order to reflect UV light 580 into the air stream.

In the embodiment shown in FIG. 5A, the UV lamp 390 is located along the side of the housing 302 and near the inlet 304. After the air passes through the inlet 304, the air is immediately exposed to UV light 580 emitted by the UV lamp 390. An elongated "U"-shaped shell 570 substantially encloses the UV lamp 390. The shell 570 has two mounts to support and electrically connect the UV lamp 390 to the power supply. The grid 392 can be located adjacent to the UV lamp 390, for example as a single piece positioned along a plane parallel to line A-A. In other embodiments, the grid 392 can be located adjacent to the UV lamp 390 along a plane askew of line A-A, for example along a plane forming a 45° angle with a plane parallel to line A-A. Positioning the grid 392 in such a way can allow a larger surface area to be both directly irradiated by the UV lamp 390 and exposed to the airflow. In still other embodiments, the grid 392 can be positioned along a plane perpendicular to line A-A. The arrangement of the grid 392 within the housing 302 can vary and can depend, for example, on the catalytic material used to coat the grid 392, the amount of UV light 580 emitted by the UV lamp 390, the location and arrangement of the UV lamp 390, the rate of airflow, the size of the grid 392, and/or the size of the housing 302, etc. One of ordinary skill in the art can appreciate the myriad different arrangements for the grid 392.

In one embodiment, shown in FIG. 5B, the shell 570 can comprise two separate surfaces. A first wall 574a is located between the UV lamp 390 and the inlet 304 and is preferably "U"-shaped, with a concave surface facing the UV lamp 390. The concave surface of the first wall 574a is preferably a non-reflective surface. Alternatively, the concave surface of the first wall 574a can reflect UV light 580 outward toward the passing airflow. It is within the scope of the present invention for the first wall 574a to have other shapes such as, but not limited to, a plate, "V"-shaped or "C"-shaped. In one embodiment the first wall 574a can be integrally formed with the removable rear panel 324 such that when the rear panel 324 is removed from the housing 302, the first wall 574a is removed, exposing the UV lamp 390. The UV lamp 390 is easily accessible to allow removal or installation of the UV lamp 390, for example.

A second wall 574b is "V"-shaped and located between the UV lamp 390 and an electrode assembly 109 to prevent a user from looking through the outlet 304 and viewing UV light 580 emitted from the UV lamp 390. The second wall 574b can have a non-reflective concave surface. Alternatively, the second wall 574b can have a reflective concave surface to reflect UV light 580 outward toward the passing airflow. It is within the scope of the present invention for the second wall 574b to have other shapes such as, but not limited to, a plate, "U"-shaped or "C"-shaped. In such embodiments, the grid 392 can comprise two sections positioned on opposite sides of, and adjacent to the UV lamp 390 such that UV light 580 emitted by the UV lamp 390 strikes the grid 392, activating the catalytic material coating the grid 392 such that the material causes VOCs within the airflow to breakdown.

The shell 570 can optionally include fins 572. The fins 572 are spaced apart and preferably substantially perpendicular to the passing airflow. In general, the fins 572 further prevent UV light 580 from shining directly towards the inlet 304 and the outlet 306. The fins 572 can have a black or non-reflective surface. Alternatively, the fins 572 can have a reflective surface. The reflective surface can prevent absorption of UV light 580 by the surfaces of the shell 570 and fins 572 and can direct more UV light 580 into the passing airflow and grid 392. The shell 570 can further include reflective surfaces to direct UV light 580 towards the fins 572, maximizing irradiation of the passing airflow and grid 392. The shell 570 and fins 572 direct the UV light 580 emitted from the UV lamp 390 in a substantially perpendicular orientation to the crossing airflow traveling through the housing 302. This prevents U light 580 from being emitted directly towards the inlet 304 or the outlet 306.

FIG. 6 illustrates yet another embodiment of the system 600. The embodiment shown in FIG. 6 is a smaller, more portable, desk version of the air transporter-conditioner. Air enters the housing 302 through an air chamber 650 (as shown by the arrows marked "IN") having multiple vertical slots 651 located along each side of the air chamber 650. In one embodiment the slots 651 are divided across the direction of airflow into the housing 302. The slots 651 preferably are spaced apart some small distance and are substantially the same height as the sidewalls of the air chamber 650. In operation, air enters the housing 302 by entering the air chamber 650 and exiting through the slots 651. Air contacts the interior surface 501 of the housing 302 and continues to travel through the housing 302 towards the outlet 304. The rear wall 653 of the air chamber 650 is a solid wall; therefore, the system 600 only requires a single surface 570 located between the UV lamp 390 and the electrode assembly 109 and outlet 306. The surface 570 is preferably "U"-shaped, having a reflective convex surface 570a facing the UV lamp 390. The reflective surface 570a redirects UV light 580 toward the interior surface 501 of the housing 302 and maximizes the dispersement of UV light 580 into the passing airflow. It is within the scope of the invention for the surface 570 to comprise other shapes such as, but not limited to, a "V"-shaped surface, or to have the concave surface 570b face the UV lamp 390. Similar to the previous embodiments, the air passes the lamp 390 and is irradiated by the UV light 580 soon after the air enters the housing 302, and prior to reaching the electrode assembly 109.

Further, the interior surface 501 can be coated with a photocatalytic material so that as air contacts the interior surface 501, VOCs are oxidized by the irradiated photocatalytic material. In other embodiments, a grid as described above having a coating of photocatalytic material can be positioned adjacent to the UV lamp 390, for example between the interior surface 501 and the UV lamp 390. In still other embodiments, a plate or other surface shaped roughly to conform to the interior surface 501 and coated with a photocatalytic material can be removably connected with or positioned close to the interior surface 501 such that air contacts the plate or other surface and VOCs within the air react with the catalytic material.

FIGS. 5A-6 illustrate embodiments of the electrode assembly 109. The electrode assembly 109 comprises a first emitter electrode array 110 and a second collector electrode array 120, which is preferably located downstream of the UV lamp 390. It is the electrode assembly 109 that creates ions and causes air to flow electro-kinetically between the first emitter electrode array 110 and the second collector electrode array 120. The first array 110 comprises two wire-shaped electrodes 112, while the second array 120 comprises three "U"-shaped electrodes 122. Each "U"-shaped electrode includes a nose and two trailing sides. It is within the scope of the invention for the first array 110 and the second array 120 to include electrodes having other shapes. For example, electrodes 122 from the second array 120 can be teardrop-shaped, "Z"-shaped, "V"-shaped, etc. Further, electrodes 112 from the first array 110, in addition to being wire-shaped, can be teardrop-shaped and can include a partially insulated surface, for example. In additional, any number of electrodes can be used, provided that each emitter electrodes 112 is spaced equidistant from a corresponding pair of adjacent collector electrodes 122. Further, the electrode assembly 109 can include interstitial electrodes, trailing electrodes, and/or focusing electrodes, etc. It is to be understood that mryiad different electrode assembly configurations can be used in the system depicted in FIGS. 2A-6.

Figure 7:
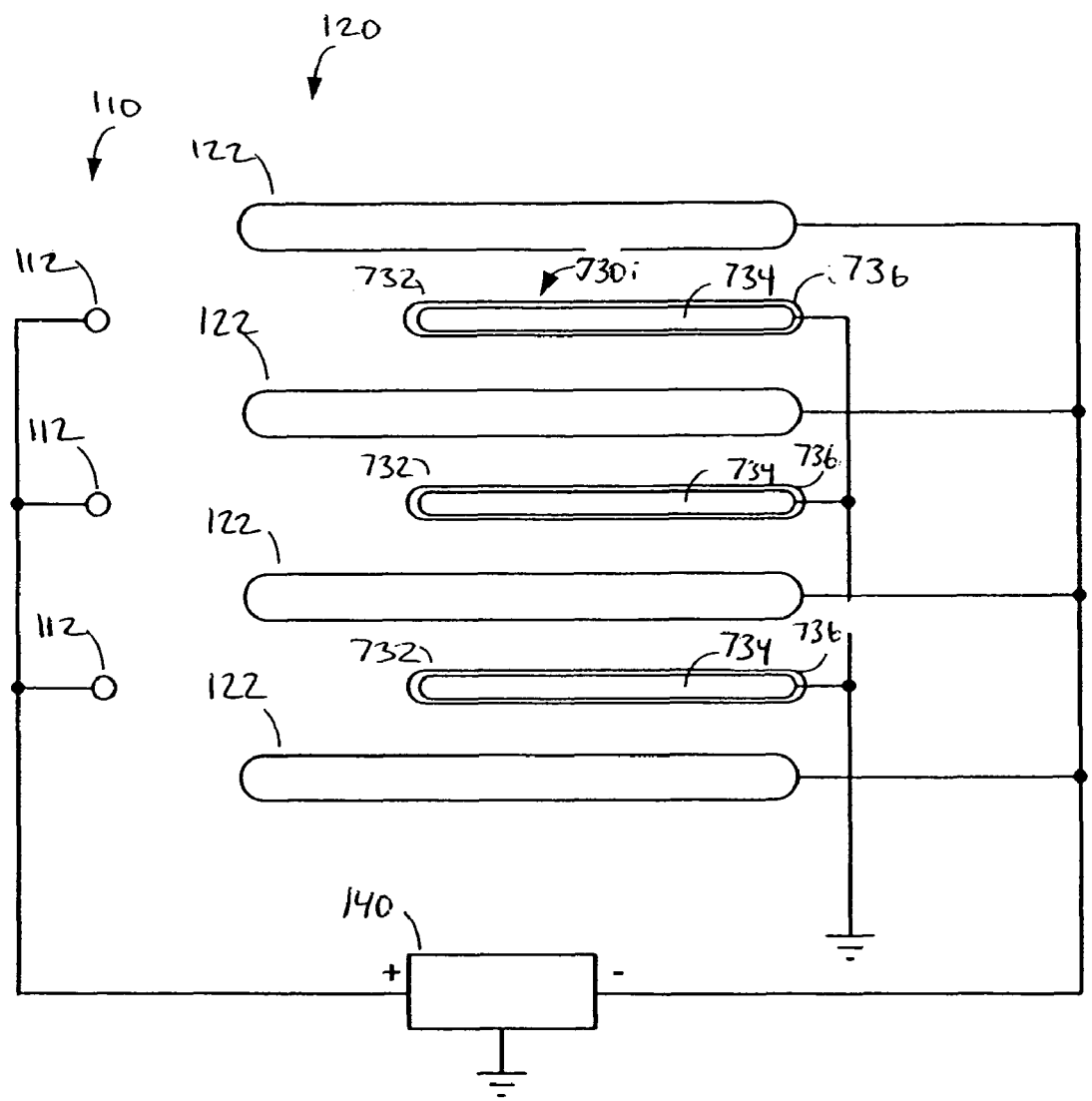
FIG. 7 is a schematic of an alternative electrode assembly for use with air transporter-conditioner systems in accordance with embodiments of the present invention.

FIG. 7 illustrates schematically an electrode assembly 109 for use with the electro-kinetic conditioner system 100 according to an alternative embodiment of the present invention. The system includes a first emitter electrode array 110 of emitter electrodes 112, a second collector electrode array 120 of collector electrodes 122 and a third array 730 of coated driver electrodes 732. In this embodiment, the first array 110 is electrically connected to a positive terminal of a high voltage source 340, and the second array 120 is electrically connected to a negative terminal of the high voltage source 140. The third array 730 of coated driver electrodes 732 is grounded and each driver electrode 732 comprises an electrically conductive electrode 734 coated by a photocatalytic material 736.

During operation of the system, the high voltage source 140 positively charges the emitter electrodes 112 and negatively charges the collector electrodes 122. For example, the voltage on the emitter electrodes 112 can be +6 KV, while the voltage on the collector electrodes 122 can be −10 KV, resulting in a 16 KV potential difference between the emitter electrodes 112 and collector electrodes 122. This potential difference produces a high intensity electric field that is highly concentrated around the emitter electrodes 112. More specifically, a corona discharge takes place from the emitter electrodes 112 to the collector electrodes 122, producing positively charged ions. Particles (e.g., dust particles) in the vicinity of the emitter electrodes 112 are positively charged by the ions. The positively charged ions are repelled by the positively charged emitter electrodes 112, and are attracted to and deposited on the negatively charged collector electrodes 122.

Further, electric fields are produced between the driver electrodes 732 and collector electrodes 122, which push the positively charged particles toward the collector electrodes 122. Generally, the greater the electric field between the driver electrodes 732 and collector electrodes 122, the greater the particle collection efficiency. Some photocatalysts, such as manganese dioxide are not electrically conductive, while others, such as activated carbon, are electrically conductive. When using a catalyst that is not electrically conductive, the driver electrodes 732 can be coated in any available manner and the coating can serve as insulation covering the driver electrodes 732, thus increasing the voltage potential difference that can be obtained between the collector electrodes 122 and the driver electrodes 732 without arcing. However, when using a photocatalyst that is electrically conductive, it is possible for arcing to occur between the collector electrodes 122 and driver electrodes 732 (as described in U.S. patent application Ser. No. 10/774,579, now U.S. Pat. No. 7,077,890, filed Feb. 9, 2004 by Botvinnik, incorporated herein by reference).

Figure 8:
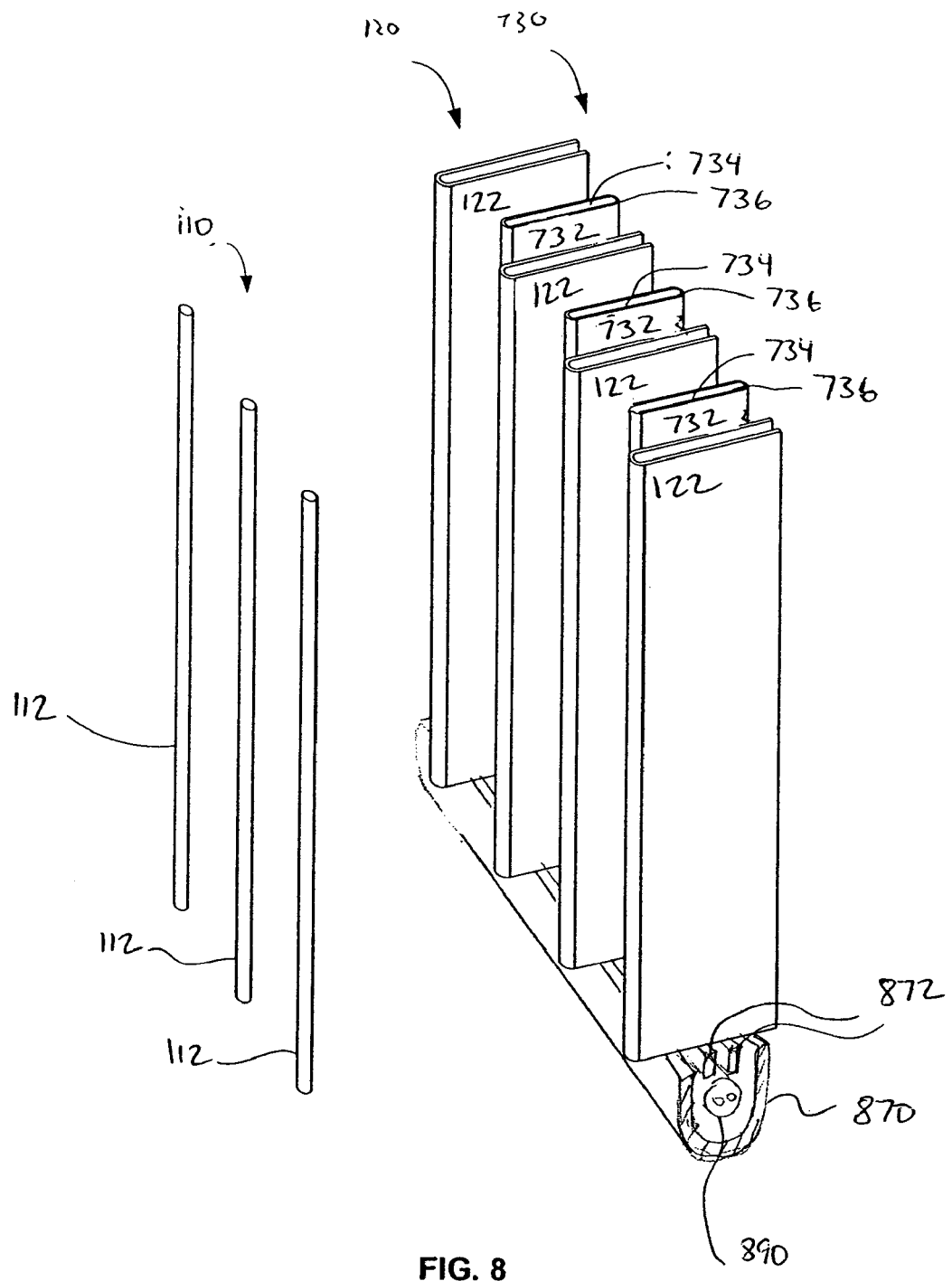
FIG. 8 is a partial perspective view of still another embodiment of the present invention, utilizing the electrode assembly of FIG. 7.

Still further, the photocatalytic material can act to breakdown VOCs in air passing between the driver electrodes 732 and collector electrodes 122. To activate the photocatalytic material, an activator, such as a UV lamp 294, should be positioned such that the driver electrodes 732 are irradiated by UV light 580 (or some other radiation having a wavelength less than 385 nm), but without allowing UV light 580 to be directly visible to a user peering through the inlet or outlet of the housing. For example, as shown in the perspective view of FIG. 8, in one embodiment the UV lamp 890 can be positioned beneath the electrode assembly 109, with the length of the UV lamp 890 positioned along an axis perpendicular to the flow of air. As with previously described embodiments, the UV lamp 890 can be substantially surrounded by a shell 870 having an inner surface that is either reflective or non-reflective. The shell 870 can include fins 872 which can also be either reflective or non-reflective. The UV lamp 890 can supplement a first UV or other germicidal lamp 390 positioned upstream of the airflow for destroying micro-organisms, or alternatively, the UV lamp 890 can substitute for the upstream UV lamp 390, killing microorganisms as air flows through the electrode assembly 109.

In addition to those described above, there are other voltage potential variations that can be used to drive an electro-kinetic system including an insulated driver electrode(s) 732. For example, the driver electrodes 732 can be electrically connected with a positive charge, rather than grounded, increasing the deflection of particles to the collector electrode 122. One of ordinary skill in the art can appreciate the myriad configurations for the electrode assembly 109.

Figure 9A:
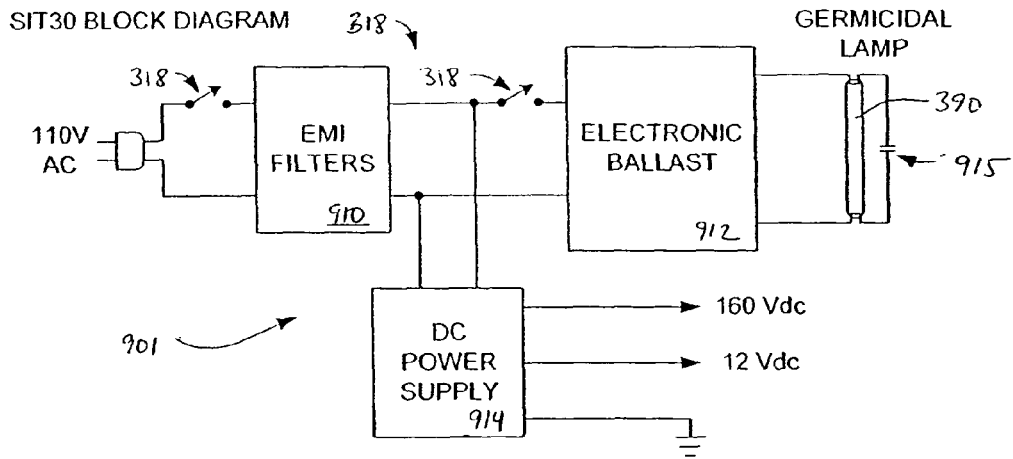
FIG. 9A is a partial electrical block diagram of an embodiment of a circuit for use with the air transporter-conditioner system of FIGS. 2A-8.
Figure 9B:
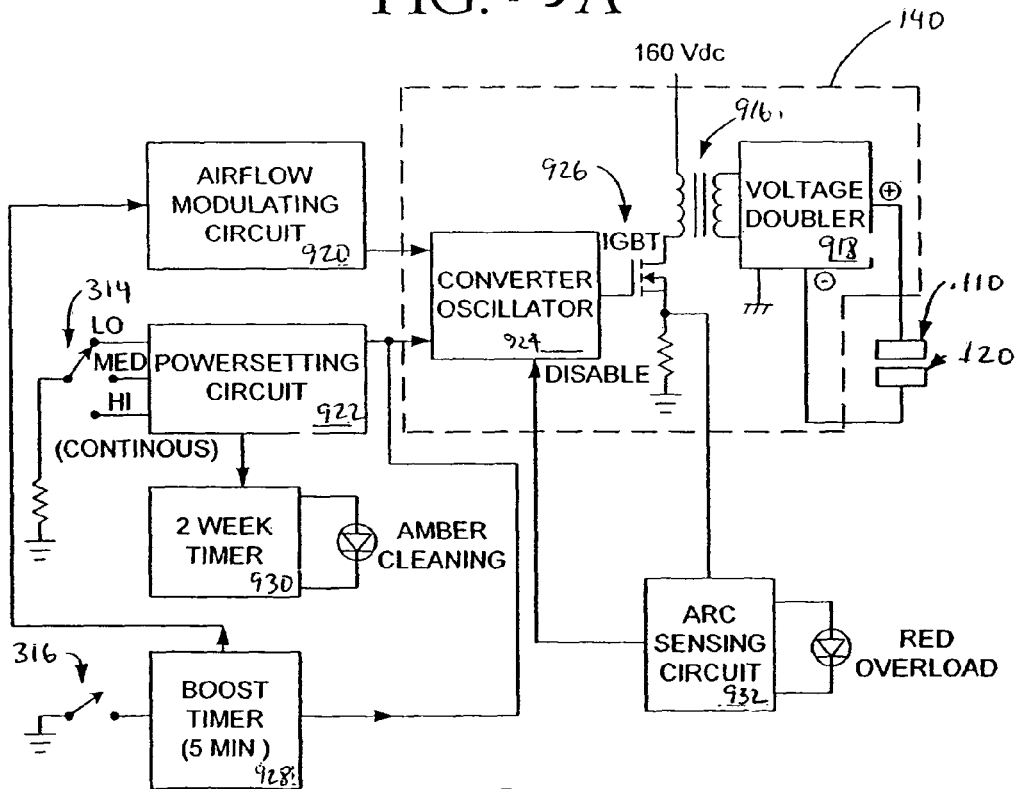
FIG. 9B is a partial electrical block diagram of a circuit for use with the circuit of FIG. 9A.

Electrical Circuit for the Air Transporter-Conditioner System:

FIGS. 9A and 9B illustrate a preferred embodiment of an electrical block diagram for the air transporter-conditioner system 300 described above. FIG. 9A illustrates a preferred electrical block diagram of the UV lamp circuit 901. The main components of the circuit 901 are an electromagnetic interference (EMI) filter 910, an electronic ballast 912, and a DC power supply 914. The system 300 has an electrical power cord that plugs into a common electrical wall socket. The (EMI) filter 910 is placed across the incoming 110 VAC line to reduce and/or eliminate high frequencies generated by the electronic ballast 912 and the DC Power Supply 914. The electronic ballast 912 is electrically connected to the UV lamp 390 to regulate, or control, the flow of current through the UV lamp 390. Electrical components such as the EMI Filter 910 and electronic ballast 912 are well known in the art and do not require a further description. The DC Power Supply 914 receives the 110 VAC and outputs 12 VDC for the internal logic of the system 300, and 160 VDC for the primary side of the transformer 916 (see FIG. 9B).

As seen in FIG. 9B, a high voltage pulse generator 140 is coupled between the first electrode array 110 and the second electrode array 120. The generator 140 receives low input voltage, e.g., 160 VDC from DC power supply 914, and generates high voltage pulses of at least 5 KV peak-to-peak with a repetition rate of about 20 KHz. Preferably, the voltage doubler 918 outputs 9 KV to the first array 110, and 18 KV to the second array 120. It is within the scope of the present invention for the voltage doubler 918 to produce a greater or smaller voltage. The pulse train output preferably has a duty cycle of perhaps 10%, but may have other duty cycles, including a 100% duty cycle. The high voltage pulse generator 140 may be implemented in many ways, and typically will comprise a low voltage converter oscillator 924, operating at perhaps 20 KHz frequency, that outputs low voltage pulses to an electronic switch. Such a switch is shown as an insulated gate bipolar transistor (IGBT) 926. The IGBT 926, or other appropriate switch, couples the low voltage pulses from the oscillator 924 to the input winding of a step-up transformer 916. The secondary winding of the transformer 916 is coupled to the voltage doubler 918, which outputs the high-voltage pulses to the first and second array of electrodes 110/120. In general, the IGBT 926 operates as an electronic on/off switch. Such a transistor is well known in the art and does not require a further description.

The voltage doubler 918 preferably includes circuitry controlling the shape and/or duty cycle of the output voltage of the generator 140. The voltage doubler 918 preferably also includes a pulse mode component, controlled by the boost timer 928, to temporarily provide a burst of increased output ozone.

The converter oscillator 924 receives electrical signals from the airflow modulating circuit 920, the power setting circuit 922, and the boost timer 928. The airflow rate of the system 300 is primarily controlled by the airflow modulating circuit 920 and the power setting circuit 922. The airflow modulating circuit 920 is a "micro-timing" gating circuit. The airflow modulating circuit 920 outputs an electrical signal that modulates between a "low" airflow signal and a "high" airflow signal. The airflow modulating circuit 920 continuously modulates between these two signals, preferably outputting the "high" airflow signal for 2.5 seconds, and then the "low" airflow signal for 5 seconds. By way of example only, the "high" airflow signal causes the voltage doubler 918 to provide 9 KV to the first array 110, while 18 KV is provided to the second array 120, and the "low" airflow signal causes the voltage doubler 918 to provide 6 KV to the first array 110, while 12 KV is provided to the second array 120. As will be described later, the voltage difference between the first and second array is proportional to the airflow rate of the system 300. In general, a greater voltage differential is created between the first and second array by the "high" airflow signal. It is within the scope of the present invention for the airflow modulating circuit 920 to produce different voltage differentials between the first and second arrays. The various circuits and components comprising the high voltage pulse generator 140 can be fabricated on a printed circuit board mounted within housing 302.

The power setting circuit 922 is a "macro-timing" circuit that can be set, by a control dial 314 (described hereinafter), to a LOW, MED, or HIGH setting. The three settings determine how long the signal generated by the airflow modulating circuit 920 will drive the oscillator 924. When the control dial 314 is set to HIGH, the electrical signal output from the airflow modulating circuit 920, modulating between the high and low airflow signals, will continuously drive the connector oscillator 924. When the control dial 314 is set to MED, the electrical signal output from the airflow modulating circuit 920 will cyclically drive the oscillator 924 for 25 seconds, and then drop to a zero or a lower voltage for 25 seconds. Thus, the airflow rate through the system 300 is slower when the dial 314 is set to MED than when the control dial 314 is set to HIGH. When the control dial 314 is set to LOW, the signal from the airflow modulating circuit 920 will cyclically drive the oscillator 924 for 25 seconds, and then drop to a zero or a lower voltage for 75 seconds. It is within the scope and spirit of the present invention for the HIGH, MED, and LOW settings to drive the oscillator 924 for longer or shorter periods of time.

The boost timer 928 sends a signal to the converter oscillator 924 when the boost button 316 is depressed. The boost timer 928 when activated, instructs the system 300 to run at a maximum airflow rate for a 5 minute period. This maximum airflow rate preferably creates an airflow velocity higher than that created when the control dial 314 is set to HIGH.

FIG. 9B further illustrates some preferred timing and maintenance features of the system 300. The system 300 has a 2 week timer 930 and an arc sensing circuit 932 that either shuts the system 300 completely off, or provides a reminder to the user to clean the system 300.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Modifications and variations can be made to the disclosed embodiments without departing from the subject and spirit of the invention as defined by the following claims. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

The invention claimed is:

1. An air transporter-conditioner, comprising:
an ion generator adapted to create an airflow, the ion generator including one or more emitter electrodes, one or more collector electrodes, and a voltage generator coupled between the one or more emitter electrodes and one or more collector electrodes;
one or more of driver electrodes located between the one or more collector electrodes, the driver electrodes being at least partially coated with a photocatalytic material;
a grid structure at least partially coated with photocatalytic material located between the one or more emitter electrodes and one or more collector electrodes; and
an activator being adapted to emit radiation onto the one or more coated driver electrodes and the grid structure, so that the photocatalytic material is activated.

2. The air transporter-conditioner of claim 1, wherein the photocatalytic material comprises a metal oxide.

3. The air transporter-conditioner of claim 2, wherein the photocatalytic material is at least one of titanium dioxide, cuprous oxide, zinc oxide, and silicon dioxide.

4. The air transporter-conditioner of claim 2, wherein the metal oxide comprises a metal selected from a group including manganese, copper, cobalt, chromium, iron, titanium, zinc and nickel.

5. The air transporter-conditioner of claim 2, wherein the photocatalytic material further comprises one or both of palladium and platinum.

6. The air transporter-conditioner of claim 1, wherein the radiation emitted by the activator has a wavelength less than 385 nm.

7. The air transporter-conditioner of claim 1, wherein the radiation emitted by the activator is in the ultraviolet spectrum.

8. The air transporter-conditioner of claim 7, wherein the activator is an ultraviolet lamp.

9. The air transporter-conditioner of claim 1, wherein the one or more coated driver electrodes are coupled to the ground.

10. The air transporter-conditioner of claim 1, wherein the one or more coated driver electrodes are coupled to a positive terminal of the voltage generator.

11. The air transporter-conditioner of claim 1, wherein the ion generator is enclosed in a housing having an inlet and an outlet.

12. The air transporter-conditioner of claim 11, further comprising a means for directing the radiation away from the inlet and the outlet.

13. The air transporter-conditioner of claim 11, wherein the housing further has an interior surface, the interior surface being a diffusing surface to minimize deflection of the radiation emitted from the activator.

14. The air transporter-conditioner of claim 13, wherein the inlet and the outlet are covered with vertically oriented fins.

15. The air transporter-conditioner of claim 1, further comprising a means to control the airflow rate.

16. The air transporter-conditioner of claim 11, wherein the housing is elongated and upstanding.

17. The air transporter-conditioner of claim 11, wherein the housing is adapted to be located on a desk.

18. The air transporter-conditioner of claim 1, wherein the ion generator is electrically connected with a power source by one of a wall plug and a car plug.

19. An air transporter-conditioner, comprising:
a housing having an inlet and an outlet;
means for creating an airflow between the inlet and the outlet wherein said means for creating comprises an emitter electrode array and a collector electrode array;
a first electrode array at least partially coated with photocatalytic material for reducing a level of volatile organic compounds within the airflow, said first electrode array being disposed within the housing; and
a grid structure at least partially coated with photocatalytic material, located between the emitter electrode array and the collector electrode array.

20. The system of claim 19, wherein a voltage potential between the emitter electrode array and the collector electrode array creates said airflow.

21. The system of claim 20, wherein said first electrode array includes one or more driver electrodes located between one or more collector electrodes.

22. The system of claim 21, wherein one or more driver electrodes are coupled to the ground.

23. The system of claim 19, further comprising means for activating disposed within the housing and arranged such that said means for activating irradiates said first electrode array.

24. The system of claim 19, wherein the photocatalytic material comprises a metal oxide.

25. The air transporter-conditioner of claim 24, wherein the photocatalytic material is at least one of titanium dioxide, cuprous oxide, zinc oxide, and silicon dioxide.

26. The air transporter-conditioner of claim 24, wherein the metal oxide comprises a metal selected from a group including manganese, copper, cobalt, chromium, iron, titanium, zinc and nickel.

27. The air transporter-conditioner of claim 24, wherein the photocatalytic material further comprises one or both of palladium and platinum.

28. The system of claim 23, wherein said means for activating irradiates said first electrode array with radiation having a wavelength less than 385 nm .

29. The system of claim 23, wherein said means for activating irradiates said first electrode array with radiation having a wavelength in the ultraviolet spectrum.

30. The system of claim 23, wherein said means for activating is an ultraviolet lamp.

31. The system of claim 23, wherein said first electrode array is located downstream from said means for activating.

32. An air transporter-conditioner system adapted to reduce volatile organic compounds within an airflow, comprising;
a housing having an inlet and an outlet;
means for generating said airflow between the inlet and the outlet, said means for generating said airflow being disposed within the housing wherein said means for creating comprises an emitter electrode array and a collector electrode array;
a first electrode array at least partially coated with photocatalytic material, said first electrode array being disposed within the housing;
a grid structure at least partially coated with photocatalytic material, located between the emitter electrode array and the collector electrode array; and
means for activating the photocatalytic material, said means for activating being arranged to irradiate said first electrode array.

33. The system of claim 32, wherein a voltage potential between the emitter electrode array and the collector electrode array generates said airflow.

34. The system of claim 33, wherein said first electrode array includes one or more driver electrodes located between one or more collector electrodes.

35. The system of claim 32, wherein the photocatalytic material comprises a metal oxide.

36. The system of claim 35, wherein the photocatalytic material is at least one of titanium dioxide, cuprous oxide, and zinc oxide.

37. The system of claim 32, wherein said means for activating irradiates said first electrode array with radiation having a wavelength less than 385 nm .

38. The system of claim 32, wherein said means for activating irradiates said first electrode array with radiation having a wavelength in the ultraviolet spectrum.

39. The system of claim 38, wherein said means for activating is an ultraviolet lamp.

40. The system of claim 32, wherein said first electrode array is located downstream from said means for activating.

41. An air transporter-conditioner, comprising;
a housing having an inlet and an outlet;
an ion generator adapted to create an airflow between the inlet and the outlet, the ion generator including an emitter electrode array, a collector electrode array, and a driver electrode array, a portion of the driver electrode array having a photocatalytic material;
a grid structure at least partially coated with photocatalytic material located between an emitter electrode array and a collector electrode array; and
an activator disposed within the housing, the activator being adapted to emit radiation onto the driver electrode array and the grid structure, so that the photocatalytic material is activated;
wherein a voltage potential between the emitter electrode array and the collector electrode array creates the airflow.

42. The air transporter-conditioner of claim 41, wherein the photocatalytic material comprises a metal oxide.

43. The air transporter-conditioner of claim 42, wherein the photocatalytic material is at least one of titanium dioxide, cuprous oxide, and zinc oxide.

44. The air transporter-conditioner of claim 41, wherein radiation emitted by the activator has a wavelength less than 385 nm.

45. The air transporter-conditioner of claim 41, wherein the radiation emitted by the activator is in the ultraviolet spectrum.

46. The air transporter-conditioner of claim 45, wherein the activator is an ultraviolet lamp.

47. The air transporter-conditioner of claim 41, wherein the driver electrode array is removably connected with the housing.

48. The air transporter-conditioner of claim 41, further comprising a means for directing the radiation away from the inlet and the outlet.

49. The air transporter-conditioner of claim 41, further comprising a means to control the airflow rate.

50. The air transporter-conditioner of claim 41, wherein the airflow rate passing the activator is slower than the airflow rate exiting the outlet.

51. The air transporter-conditioner of claim 41, wherein the housing further has an interior surface, the interior surface being a diffusing surface to minimize deflection of the radiation emitted from the activator.

52. The air transporter-conditioner of claim 51, wherein the inlet and the outlet are covered with vertically oriented fins.

53. An air transporter-conditioner, comprising;
a housing having an inlet and an outlet;
an ion generator adapted to create an airflow between the inlet and the outlet, the ion generator including an emitter electrode array, a collector electrode array, and a driver electrode array, wherein one or more driver electrodes being coated with a photocatalytic material;
a grid structure at least partially coated with photocatalytic material located between an emitter electrode array and a collector electrode array; and
an activator disposed within the housing, the activator being adapted to emit radiation onto the driver electrode array and the grid structure, so that the photocatalytic material is activated.

54. The air transporter-conditioner of claim 53, wherein a voltage potential between the emitter electrode array and the collector electrode array creates the airflow.

55. The air transporter-conditioner of claim 53, wherein the photocatalytic material comprises a metal oxide.

56. The air transporter-conditioner of claim 55, wherein the photocatalytic material is at least one of titanium dioxide, cuprous oxide, and zinc oxide.

57. The air transporter-conditioner of claim 53, wherein the radiation emitted by the activator has a wavelength less than 385 nm .

58. The air transporter-conditioner of claim 53, wherein the radiation emitted by the activator is in the ultraviolet spectrum.

59. The air transporter-conditioner of claim 58, wherein the activator is an ultraviolet lamp.

60. The air transporter-conditioner of claim 53, wherein the driver electrode array is removably connected with the housing.

61. The air transporter-conditioner of claim 53, further comprising a means for directing the radiation away from the inlet and the outlet.

62. The air transporter-conditioner of claim 53, further comprising a means to control the airflow rate.

63. The air transporter-conditioner of claim 53, wherein the airflow rate passing the activator is slower than the airflow rate exiting the outlet.

64. The air transporter-conditioner of claim 53, wherein the housing further has an interior surface, the interior surface being a diffusing surface to minimize deflection of the radiation emitted from the activator.

65. The air transporter-conditioner of claim 64, wherein the inlet and the outlet are covered with vertically oriented fins.

66. A method for air conditioning, comprising:
providing an ion generator adapted to create an airflow, the ion generator including one or more emitter electrodes, one or more collector electrodes, one or more of driver electrodes located between the one or more collector electrodes, and a grid structure located between the one or more emitter electrodes and one or more collector electrodes, wherein the driver electrodes and the grid structure being at least partially coated with a photocatalytic material; and
activating said ion generator such that a voltage potential exists between the one or more emitter electrodes and the one or more collector electrodes so that an airflow is created; and
emiting radiation onto the one or more coated driver electrodes and the grid structure, so that the photocatalytic material is activated.

67. The method of claim 66, further comprising activating said ion generator such that a voltage potential exists between the one or more emitter electrodes and the one or more driver electrodes.

68. The method of claim 66, further comprising activating said ion generator such that a voltage potential exists between the one or more collector electrodes and the one or more driver electrodes.

* * * * *